US006277594B1

(12) United States Patent
Mikoshiba et al.

(10) Patent No.: US 6,277,594 B1
(45) Date of Patent: Aug. 21, 2001

(54) NEUROGENESIS INDUCING GENE

(75) Inventors: Katsuhiko Mikoshiba, Saitama; Jun Aruga, Ibaraki; Takeharu Nagai, Ibaraki; Katsunori Nakata, Ibaraki, all of (JP)

(73) Assignee: The Institute of Physical and Chemical Research, Saitama (JP)

( * ) Notice: Subject to any disclaimer, the term of this patent is extended or adjusted under 35 U.S.C. 154(b) by 0 days.

(21) Appl. No.: 09/172,045

(22) Filed: Sep. 28, 1998

(30) Foreign Application Priority Data

Mar. 31, 1998 (JP) .................................. 10-086979
Apr. 30, 1998 (JP) .................................. 10-121456

(51) Int. Cl.$^7$ .............................. C12P 21/06; C12N 1/20; C12N 5/00; C12N 15/88; C07H 21/04
(52) U.S. Cl. ..................... 435/69.1; 435/252.3; 435/325; 435/458; 435/320.1; 536/23.5
(58) Field of Search .................................. 536/23.1, 23.5; 514/44; 435/69.1, 252.3, 325, 320.1

(56) References Cited

PUBLICATIONS

Verma et al. Nature 389: 239–242, especially p. 239, Sep. 1997.*
Anderson et al. Nature 392: 25–30, especially pp. 25 and 30, Apr. 199.*
Eck and Wilson. In Goodman and Gilmans the Pharmacological basis of Therapeutics. McGraw–Hill publishers. pp. 77–101, especially 77–82, in particular p. 81 column 2 to p. 82 column 2, 1995.*
Upton et al. Mol Endocrinol 9: 83–92, abstract only, Aug. 1992.*
Frade et al. Development 122: 2497–2506, see especially lines 1–4 of abstract, Aug. 1996.*
Aruga et al. J Neurochem 63: 1880–1890, see especially Fig. 1, p. 1882, 1994.*
Aruga et al. GenEmbl Accession No. D32167, Jul. 1994.*
Aruga et al., "The mouse Zic gene family Homologues of the Drosophila pair–rule gene odd–paired," *J. Biol. Chem.* 271: 1043–1047 [1996].
Becker et al., "High–efficiency transformation of yeast by electroporation," *Methods Enzymol.*, 194:182–187 [1990].
Benedyk et al., "Odd–paired: a zinc finger pair–rule protein required for the timely activation of engrailed and wingless in Drosophila embryos," *Genes Dev.*, 8:105–117 [1994].
Chitnis et al., "Primary neurogenesis in Xenopus embryos regulated by a homologue of the Drosophila neurogenic gene Delta," *Nature* 375:761–766 [1995].
Cohen et al., "Nonchromosomal antibiotic resistance in bacteria: genetic transformation of *Escherichia coli* by R–Factor DNA," *Proc. Natl. Acad. Sci. USA* 69:2110–2114 [1972].
Ferreiro et al., "XASH genes promote neurogenesis in Xenopus embryos," *Development* 120:3649–3655 [1994].

Godsave et al., "Clonal analysis of mesoderm induction in *Xenopus laevis*," *Dev. Biol.* 134:486–490 [1989].
Grunz et al., "Neural differentiation of *Xenopus laevis* ectoderm takes place after disaggregation and delayed reaggregation without inducer," *Cell Differ. Dev.* 28:211–218 [1989].
Hanahan, "Studies on transformation of *Escherichia coli* with plasmids," *J. Mol. Bio.*, 166:557–580 [1983].
Harland, "In situ hybridization: an improved whole–mount method for Xenopus embryos," *Methods in Cell Biol.*, 36:685–694 [1991].
Hemmati–Brivanlou et. al., "Cephalic expression and molecular characterization of *Xenopus en–2*," *Development* 111(3):715–724 [1991].
Hemmati–Brivanlou et al., "Follistatin, an antagonist of activin, is expressed in the Spemann Organizer and displays direct neuralizing activity," *Cell* 77:283–295 [1994].
Hinnen et al., "Transformation of yeast," *Proc. Natl. Acad. Sci. USA* 75:1929–1933 [1978].
Ito et al., "Transformation of intact yeast cells treated with alkali cations," *J. Bacteriol.*, 153:163–168 [1983].
Jones and Woodland, "Development of the ectoderm in Xenopus: tissue specification and the role of cell association and division," *Cell* 44:345–355 [1986].
Kintner and Melton, "Expression of Xenopus N–CAM RNA in ectoderm is an early response to neural induction," *Development* 99:311–325 [1987].
Lamb et al., "Neural induction by the secreted polypeptide Noggin," *Science* 262:713–718 [1993].
Lee et al., "Conversion of Xenopus ectoderm into neurons by NeuroD, a basic helix–loop–helix protein," *Science* 268:836–844 [1995].
Newport et al., "A major developmental transition in early Xenopus embryos: I. characterization and timing of cellular changes at the midblastula stage," *Cell* 30:675–686 [1982].
Oschwald et al., "Localization of a nervous system–specific class II β–tubulin gene in *Xenopus laevis* embryos by whole–mount in situ hybridization," *Int. J. Dev. Biol.* 35:399–405 [1991].
Pearson et al., "Improved tools for biological sequence comparison," *Proc. Natl. Acad. Sci. USA* 85:2444–2448 [1988].

(List continued on next page.)

*Primary Examiner*—Karen M. Hauda
*Assistant Examiner*—Richard Schnizer
(74) *Attorney, Agent, or Firm*—Medlen & Carroll, LLP

(57) ABSTRACT

A neurogenesis inducing gene coding for the following protein (a) or (b):

(a) a protein consisting of the amino acid sequence shown in SEQ ID NO: 2

(b) a protein which consists of the amino acid sequence shown in SEQ ID NO: 2 having deletion, substitution or addition of at least one amino acid and which has neurogenesis inducing activity.

9 Claims, 6 Drawing Sheets

(4 of 6 Drawing Sheet(s) Filed in Color)

OTHER PUBLICATIONS

Sambrook et al., *Molecular Cloning: A Laboratory Manual*, 2nd ed., Cold Spring Harbor Laboratory Press, New York, 18.3–18.18 [1989].

Sasai et al., "*Xenopus chordin*: a novel dorsalizing factor activated by organizer–specific homeobox genes," *Cell* 79:779–790 [1994].

Sasai et al., "Regulation of neural induction by the Chd and Bmp–4 antagonistic patterning signals in Xenopus," *Nature* 376:333–336 [1995].

Shain and Zuber, "Sodium dodecyl sulfate (SDS)–based whole mount in situ hybridization of *Xenopus laevis* embryos," *J. Biochem. Biophys. Methods* 31:185–188 [1996].

Suzuki et al., "Bone morphogenic protein acts as a ventral mesoderm modifier in early Xenopus embryos," *Develop. Growth Differ.*, 37:581–588 [1995].

Takebayashi et al., "Conversion of ectoderm into a neural fate by ATH–3, a vertebrate basic helix–loop–helix gene homologous to Drosophila proneural gene atonal," *EMBO J.*, 16:384–395 [1997].

Turner and Woodland, "H3 and H4 histone cDNA sequences from Xenopus: a sequence comparison of H4 genes," *Nucleic Acids Res.*, 10:3769–3780 [1982].

Turner and Weintraub, "Expression of achaete–scute homolog 3 in Xenopus embryos converts ectodermal cells to a neural fate," *Genes Dev.*, 8:1434–1447 [1994].

Wilson and Hemmati–Brivanlou, "Induction of epidermis and inhibition of neural fate by Bmp–4," *Nature* 376:331–333 [1995].

Witta et al., "XIPOU2, a noggin–indudible gene, has direct neuralizing activity," *Development* 121:721–730 [1995].

Wright et al., "The Xenopus XIHbox 6 homeo protein, a marker of posterior neural induction, is expressed in proliferating neurons," *Development* 109:225–234 [1990].

Zimmerman et al., "XASH–3, a novel *Xenopus achaete–scute* homolog, provides an early marker of planar neural induction and position along the mediolateral axis of the neural plate," *Development* 119:221–231 [1993].

Zimmerman et al., "The Spemann Organizer signal noggin binds and inactivates bone morphogenic protein 4," *Cell* 86:599–606 [1996].

Mizuseki et al., "Xenopus Zic–related–1 and Sox–2, two factors induced by chordin, have distinct activities in the initiation of neural induction," *Development* 125, 579–587 [1998].

Aruga et al., "A novel zinc finger protein, Zic, is involved in neurogenesis, especially in the cell lineage of cerebellar granule cells," *J. Neurochem.*, 63:1880–1890 [1994].

Aruga et al., "Mouse Zic1 is involved in cerebellar development," *J. Neurosci.*, 18:284–293 [1998].

Aruga et al., "Identification and characterization of Zic4, a new member of the mouse Zic gene family," *Gene* 172:291–294 [1996].

Nagai et al., "The expression of the mouse Zic1, Zic2 and Zic3 gene suggests an essential role for Zic genes in body pattern formation," *Dev. Biol.* 182:299–313 [1997].

Gebbia et al., "X–linked situs abnormalities result from mutations in ZIC3," *Nature Genet.*, 17:305–308 [1997].

Cimbora and Sakonju, "Drosophila midgut morphogenesis requires the function of the segmentation gene odd–paired," *Dev. Biol.*, 169:580–595 [1995].

Yokota et al., "Predominant expression of human Zic in cerebellar granule cell lineage and medulloblastoma," *Cancer Res.*, 56:377–383 [1996].

Nakata et al., "Xenopus Zic3, a primary regulator both in neural and neural crest development," *Proc. Natl. Acad. Sci. USA* 94:11980–11985 [1997].

Nakata et al., "Xenopus Zic family and its role in neural and neural crest development," *Mechanisms of Development* 75:43–51 [1998].

* cited by examiner

NEUROGENESIS INDUCING GENE

This application claims priority benefit to Japanese patent application numbers 86979/1998, filed Mar. 31, 1998, and 121456/1998, filed Apr. 30, 1998.

FIELD OF THE INVENTION

The present invention relates to a neurogenesis inducing gene.

BACKGROUND OF THE INVENTION

The early process of vertebrate neurogenesis is divided into several basic processes, such as differentiation into the neural plate (neural induction) and formation and maturation of the neural network from the ectoderm. This early process includes the appearance of neural precursor cells, pattern formation of the nervous system, and proliferation and differentiation of neural precursor cells. For the understanding of the molecular basis of higher brain functions, it is important to elucidate the universal, underlying principles of these processes in all species.

It is known that the early neurogenesis of *Xenopus laevis* is induced by blockade of BMP4 (Bone Morphogenetic Protein 4) signals by noggin, chordin, etc. secreted by the organizer [Sasai, Y. et al.: Nature, 376:333 (1995)]. BMP4 is a factor which induces the ectoderm into epidermal cells; under a condition where BMP4 is activated, cells differentiate into the epidermis.

On the other hand, as genes involved in the control of neural induction (neurogenesis, neural differentiation) which are called proneural genes, Neurogenin, NeuroD, XASH-3, XATH-3 and the like coding for basic-helix-loop-helix (bHLH) transcription factors are known.

However, it is still unknown what regulates the cascade linking the blockage of BMP4 signals to proneural genes.

SUMMARY OF THE INVENTION

It is an object of the present invention to provide a neurogenesis inducing protein; a gene coding for the protein; a recombinant vector comprising the gene; a transformant comprising the vector; an antibody against the protein; and a therapeutic agent for diseases of the nervous system.

As a result of extensive and intensive research toward the solution of the above problem, the present inventors have succeeded in isolating a gene having neurogenesis inducing activity from a Xenopus neurula CDNA library. Thus, the present invention has been achieved.

The present invention relates to the following recombinant protein (a) or (b):
(a) a protein consisting of the amino acid sequence shown in SEQ ID NO: 2
(b) a protein which consists of the amino acid sequence shown in SEQ ID NO: 2 having deletion, substitution or addition of at least one amino acid and which has neurogenesis inducing activity.

Further, the present invention relates to a neurogenesis inducing gene coding for the following protein (a) or (b):
(a) a protein consisting of the amino acid sequence shown in SEQ ID NO: 2
(b) a protein which consists of the amino acid sequence shown in SEQ ID NO: 2 having deletion, substitution or addition of at least one amino acid and which has neurogenesis inducing activity;
or a gene which hybridizes with the above gene under stringent conditions and which codes for a protein having neurogenesis inducing activity.

Further, the present invention relates to a gene consisting of the following DNA (c) or (d):
(c) a DNA consisting of the nucleotide sequence shown in SEQ ID NO: 1
(d) a DNA which hybridizes with the DNA consisting of the nucleotide sequence of (c) under stringent conditions and which codes for a protein having neurogenesis inducing activity.

Further, the present invention relates to a recombinant vector comprising any of the genes described above.

Further, the present invention relates to a transformant comprising the above vector.

Further, the present invention relates to a method for producing a neurogenesis inducing protein, comprising culturing the above transformant and recovering the neurogenesis inducing protein from the resultant culture.

Further, the present invention relates to an antibody against the above protein.

Further, the present invention relates to a therapeutic agent for diseases of the nervous system comprising the above protein as an active ingredient, or an agent for gene therapy for nervous diseases comprising the above gene. As the nervous disease, at least one disease selected from the group consisting of Alzheimer's disease, amyotrophic lateral sclerosis, spinocerebellar degeneration, Parkinson's disease and cerebral ischemia may be given.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

DETAILED DESCRIPTION OF THE PREFERRED EMBODIMENTS

Figure 1:
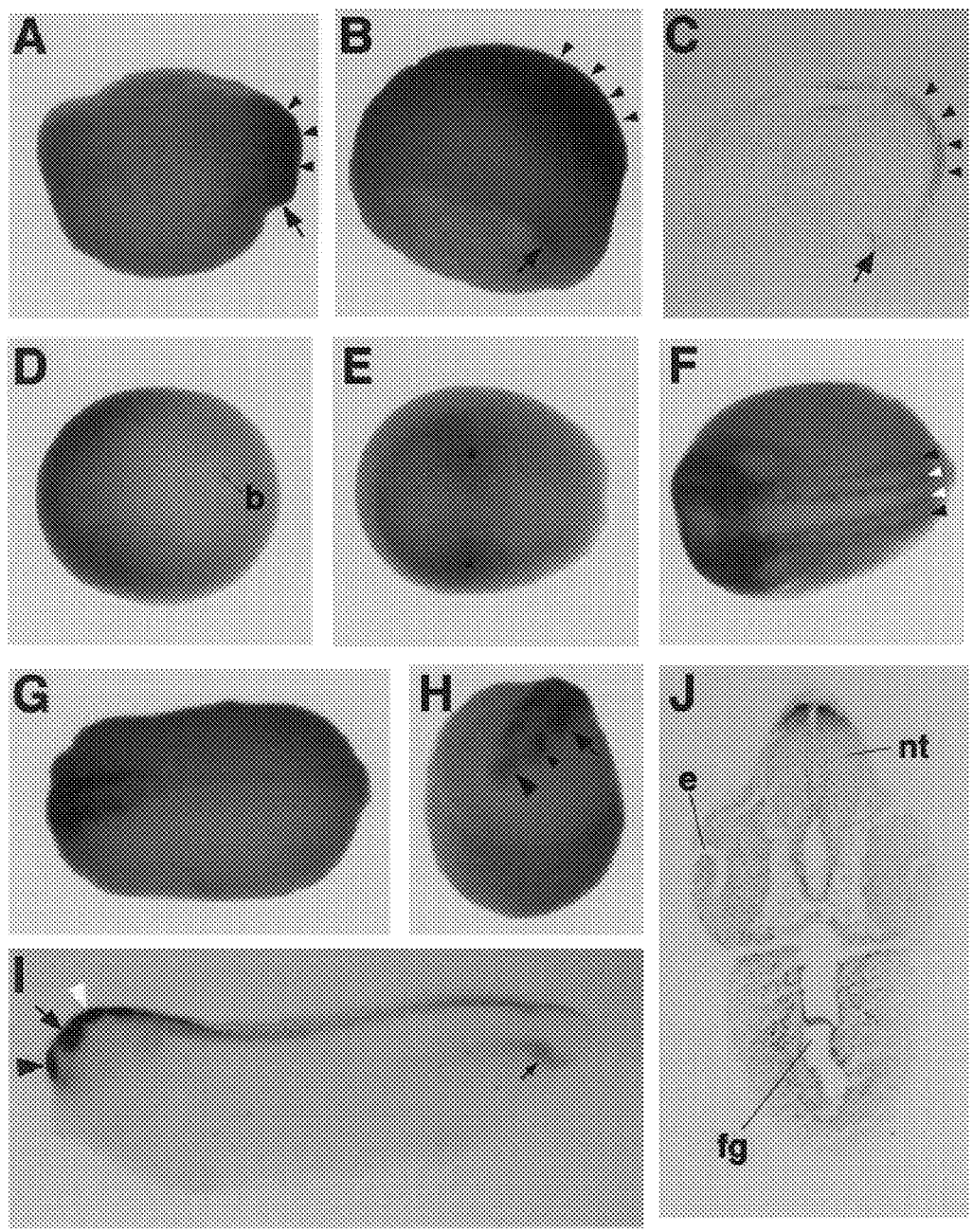
FIGS. 1A–1J present photographs showing the results of expression analysis of the Zic3 gene of the invention (morphology of an organism).

Hereinbelow, the present invention will be described in detail.

The gene of the present invention has a function to induce neurogenesis, preferably early neurogenesis, and is also called a master gene. The gene of the present invention is sometimes referred to as "Zic3".

The gene of the present invention can be cloned as described below.

1. Cloning of the Zic3 Gene (1) Preparation of a CDNA Library and Screening Thereof As a source of mRNA, a *Xenopus laevis* tissue such as the neurula may be given.

mRNA can be prepared by conventional methods. For example, the above-mentioned tissue or cells are treated with a guanidine reagent, phenol reagent or the like to obtain the total RNA. Subsequently, poly(A+)RNA (mRNA) can be obtained therefrom by the affinity column method using oligo dT-cellulose or poly U-Sepharose carried on Sepharose 2B or by the batch method. Further, the resultant poly(A+)RNA may be further fractionated by sucrose gradient centrifugation or the like.

A single-stranded cDNA is synthesized using the thus obtained mRNA as a template, an oligo(dT) primer and a reverse transcriptase. Then, a double-stranded cDNA is synthesized from the resultant single-stranded cDNA. The resultant double-stranded cDNA is integrated into an appropriate cloning vector to prepare a recombinant vector. A cDNA library can be obtained by transforming *Escherichia coli* or the like with the resultant recombinant vector and selecting the transformant using tetracycline or ampicillin resistance as an indicator.

The transformation of *E. coli* can be performed by the method of Hanahan [Hanahan, D.: J. Mol. Biol. 166:557–580 (1983)] or the like. Briefly, a method in which a recombinant vector is added to competent cells prepared under the co-existence of calcium chloride, magnesium chloride or rubidium chloride may be used. When a plasmid is used as a vector, the plasmid should contain a drug resistance gene such as tetracycline or ampicillin resistance. Alternatively, a cloning vector other than plasmids, e.g. λ phage or the like may be used.

As a screening method to select clones containing the DNA of interest from the resultant transformants, a method may be given, for example, in which a sense primer and an anti-sense primer corresponding to the amino acid sequence of the zinc finger motif of the mouse Zic gene family are synthesized and a polymerase chain reaction (PCR) is performed using these primers.

As a template DNA to be used in the above PCR, a cDNA which is synthesized from the above-described mRNA by reverse transcription may be given. As primers, 5'-GAGAACCTCAAGATCCACAA-3' (SEQ ID NO: 5) synthesized based on Glu Asn Leu Lys Ile His Lys (SEQ ID NO: 3) may be used for the sense strand; and 5'-TT(C/T)CCATG(A/G)ACCTTCATGTG-3' (SEQ ID NO: 6) synthesized based on His Met Lys Val His Glu Glu (SEQ ID NO: 4) may be used for the anti-sense strand, for example. In the present invention, however, primers are not limited to these ones.

The amplified DNA fragment obtained by the above procedures is labelled with $^{32}$P, 35S or biotin to obtain a probe. This probe is hybridized to a nitrocellulose filter on which the DNA of the transformant is denatured and fixed. Then, screening can be performed by searching for positive clones.

(2) Determination of the Nucleotide Sequence

For the resultant clone, the nucleotide sequence is determined. This sequencing can be performed by conventional methods such as the chemical modification method of Maxam-Gilbert or the dideoxynucleotide chain termination method using M13 phage. Usually, the sequencing is carried out with an automated DNA sequencer (e.g. Perkin-Elmer Model 373A DNA Sequencer).

SEQ ID NO: 1 illustrates by example a nucleotide sequence for the gene of the invention, and SEQ ID NO: 2 illustrates by example an amino acid sequence for the protein of the invention. As long as a protein consisting of this amino acid sequence retains neurogenesis inducing activity, in particular early neurogenesis inducing activity, the amino acid sequence may contain mutations, such as deletions, substitutions or additions, of at least one amino acid.

For example, at least 1 amino acid, preferably 1 to about 10 amino acids, more preferably 1 to 5 amino acids may be deleted in the amino acid sequence shown in SEQ ID NO: 2; or at least 1 amino acid, preferably 1 to about 10 amino acids, more preferably 1 to 5 amino acids may be added to the amino acid sequence shown in SEQ ID NO: 2; or at least 1 amino acid, preferably 1 to about 10 amino acids, more preferably 1 to 5 amino acids may be substituted with other amino acid(s) in the amino acid sequence shown in SEQ ID NO: 2.

Accordingly, a gene coding for a polypeptide having the amino acid sequence into which the above-mentioned mutation has been introduced is included in the gene of the invention as long as it has neurogenesis inducing activity (e.g. early neurogenesis inducing activity).

Also, a DNA which can hybridize with the gene described above under stringent conditions is included in the gene of the invention. The "stringent conditions" means, for example, those conditions in which sodium concentration is 600–900 mM and temperature is 60–68° C., preferably 65° C.

In the term "early neurogenesis" used herein, "early" means up to the formation of the neural plate from the ectoderm (i.e., from the late blastula stage to the neurula stage of Xenopus embryos), and "neurogenesis" means the process of neurogenesis as a whole including development, differentiation and maturation of the nervous system after the early neurogenesis. Also, the term "early neurogenesis inducing activity" means an activity which gives rise to the neural plate and other tissues related thereto (e.g. neural crest) from the ectoderm.

The introduction of mutation into a gene may be performed by conventional methods such as the method of Kunkel, the gapped duplex method, or variations thereof using a mutation introducing kit [e.g. Mutant-K (Takara) or Mutant-G (Takara)] utilizing site-specific mutagenesis or using a LA PCR in vitro Mutagenesis Series Kit manufactured by Takara.

Once the nucleotide sequence of the gene of the invention has been determined definitely, the gene of the invention can be obtained by chemical synthesis, by PCR using the cDNA or genomic DNA of the gene of the invention as a template, or by hybridization of a DNA fragment having the above nucleotide sequence as a probe.

2. Preparation of a Recombinant Vector and a Transformant (1) Preparation of a Recombinant Vector The recombinant vector of the invention can be obtained by ligating (inserting) the gene of the invention to (into) an appropriate vector. The vector into which the gene of the invention is to be inserted is not particularly limited as long as it is replicable in a host. For example, plasmid DNA, phage DNA or the like may be used.

Specific examples of plasmid DNA include *E. coli*-derived plasmids (e.g. pBR322, pBR325, pUC118, pUC119, etc.), *Bacillus subtilis*-derived plasmids (e.g. pUB110, pTP5, etc.) and yeast-derived plasmids (e.g. YEp13, YEp24, YCp50, etc.). Specific examples of phage DNA include λ phage and the like. Further, an animal virus vector such as retrovirus or vaccinia virus; or an insect virus vector such as baculovirus may also be used.

For insertion of the gene of the invention into a vector, a method may be employed in which the purified DNA is digested with an appropriate restriction enzyme and then inserted into the restriction site or the multi-cloning site of an appropriate vector DNA for ligation to the vector.

The gene of the invention should be operably linked to the vector. For this purpose, the vector of the invention may contain, if desired, cis elements such as an enhancer, splicing signal, poly(A) addition signal, selection marker, ribosome binding sequence (SD sequence) or the like in addition to a promoter and the gene of the invention. As the selection marker, dihydrofolate reductase gene, ampicillin resistance gene, neomycin resistance gene, or the like may be enumerated.

(2) Preparation of a Transformant

The transformant of the invention can be obtained by introducing the recombinant vector of the invention into a host so that the gene of interest can be expressed. The host is not particularly limited as long as it can express the DNA of the invention. Specific examples of the host include Escherichia bacteria such as *E. coli*; Bacillus bacteria such as *Bacillus subtilis*; Pseudomonas bacteria such as *Pseudomonas putida*; Rhizobium bacteria such as *Rhizobium meliloti*; yeasts such as *Saccharomyces cerevisiae*, *Schizosaccharomyces pombe*; animal cells such as COS cells, CHO cells; or insect cells such as Sf9 cells, Sf21 cells.

When a bacterium such as *E. coli* is used as the host, the recombinant vector of the invention is capable of autonomous replication in the host and, at the same time, it is constituted preferably by a promoter, a ribosome binding sequence, the gene of the invention and a transcription termination sequence. The vector may also contain a gene to control the promoter.

As *E. coli*, K12 or DH1 strain may be used, for example. As *Bacillus subtilis*, MI 114 or 207-21 strain may be used, for example.

As the promoter, any promoter may be used as long as it can direct the expression of the gene of interest in a host such as *E. coli*. For example, an *E. coli*- or phage-derived promoter such as trp promoter, lac promoter, $P_L$ promoter or $P_R$ promoter may be used. An artificially designed and altered promoter such as tac promoter may also be used.

As a method for introducing the recombinant vector into a bacterium, any method of DNA introduction into bacteria may be used. For example, a method using calcium ions [Cohen, S. N. et al., Proc. Natl. Acad. Sci., USA, 69:2110–2114 (1972)], electroporation, or the like may be used.

When a yeast is used as the host, *Saccharomyces cerevisiae, Schizosaccharomyces pombe, Pichia pastoris* or the like is used. In this case, the promoter to be used is not particularly limited. Any promoter may be used as long as it can direct the expression of the gene of interest in yeast. For example, gall promoter, ga110 promoter, heat shock protein promoter, MF α1 promoter, PH05 promoter, PGK promoter, GAP promoter, ADH promoter, AOX1 promoter or the like may be enumerated.

As a method for introducing the recombinant vector into the yeast, any method of DNA introduction into yeasts may be used. For example, electroporation [Becker, D. M. et. al, Methods Enzymol., 194:182–187 (1990)], the spheroplast method [Hinnen, A. et al., Proc. Natl. Acad. Sci., USA, 75:1929–1933 (1978)], the lithium acetate method [Ito, H., J. Bacteriol., 153:163–168 (1983)] or the like may be enumerated.

When an animal cell is used as the host, simian COS-7 or Vero cells, Chinese hamster ovary cells (CHO cells), mouse L cells, rat GH3 cells, human FL cells or the like may be used. As a promoter, SR α promoter, SV40 promoter, LTR promoter, CMV promoter or the like may be used. The early gene promoter of human cytomegalovirus may also be used.

As a method for introducing the recombinant vector into the animal cell, electroporation, the calcium phosphate method, lipofection or the like may be enumerated.

When an insect cell is used as the host, Sf9 cells, Sf21 cells or the like may be used.

As a method for introducing the recombinant vector into the insect cell, the calcium phosphate method, lipofection, electroporation or the like may be enumerated.

The recombinant vector of the invention incorporated in *E. coli* DH5 (designation: *Escherichia coli* pxenopus Zic3) was deposited at the National Institute of Bioscience and Human-Technology, Agency of Industrial Science and Technology (1–3, Higashi 1-Chome, Tsukuba City, Ibaraki Pref., Japan) as FERM BP-6519 under the Budapest Treaty on Mar. 26, 1998.

3. Analysis of the Time of Expression of the Zic3 Gene and the Site of Expression thereof in the Embryo Since the gene of the invention has neurogenesis inducing activity, the expression of this gene can be examined by using embryos of specific developmental stages.

The time of expression of the Zic3 gene of the invention in the embryo can be confirmed by analyzing, for example, expression of the MRNA or the protein in embryos of defined developmental stages. For example, as a method for confirming expression of Zic3 mRNA, RT-PCR or northern analysis may be used; as a method for confirming expression of ZIC3 protein, western analysis using an antibody against this protein may be used.

Further, the distribution of Zic3 expression in the embryo can be confirmed by analyzing the mRNA by in situ hybridization or the like, or by analyzing the protein by immunohistochemical techniques using an antibody. In situ hybridization can be performed, for example, as described previously [Chitnis, A. et al., Nature 375:761–766 (1995)] by staining the embryo as it is with digoxigenin or a radio isotope labelled RNA prove.

4. Production of the Protein of the Invention

The protein of the invention is a protein having the amino acid sequence encoded by the Zic3 gene of the invention, or a protein which has the above amino acid sequence having the mutation described above at least at 1 amino acid and which has neurogenesis inducing activity. The protein of the invention is also called "ZIC3 protein".

ZIC3 protein of the invention can be obtained by culturing the transformant described above and recovering the protein from the resultant culture. The term "culture" means any of the following materials: culture supernatant, cultured cells, cultured microorganisms, or crushed cells or microorganisms.

The cultivation of the transformant of the invention in a medium is carried out by conventional methods used for culturing a host.

As a medium to culture the transformant obtained from a microorganism host such as *E. coli* or yeast, either a natural or a synthetic medium may be used as long as it contains carbon sources, nitrogen sources and inorganic salts assimilable by the microorganism and is capable of effective cultivation of the transformant.

As carbon sources, carbohydrates such as glucose, fructose, sucrose, starch; organic acids such as acetic acid, propionic acid; and alcohols such as ethanol and propanol may be used.

As nitrogen sources, ammonia; ammonium salts of inorganic or organic acids such as ammonium chloride, ammonium sulfate, ammonium acetate, ammonium phosphate; other nitrogen-containing compounds; Peptone; meat extract; corn steep liquor and the like may be used.

As inorganic substances, potassium dihydrogen phosphate, dipotassium hydrogen phosphate, magnesium phosphate, magnesium sulfate, sodium chloride, iron(II) sulfate, manganese sulfate, copper sulfate, calcium carbonate and the like may be used.

Usually, the cultivation is carried out under aerobic conditions (such as shaking culture or aeration agitation culture) at 37° C. for 6 to 24 hrs. During the cultivation, the pH is maintained at 7.0 to 7.5. The pH adjustment is carried out using an inorganic or organic salt, an alkali solution or the like.

During the cultivation, an antibiotic such as ampicillin or tetracycline may be added to the medium if necessary.

When a microorganism transformed with an expression vector using an inducible promoter is cultured, an inducer may be added to the medium if necessary. For example, when a microorganism transformed with an expression vector using Lac promoter is cultured, isopropyl-β-D-thiogalactopyranoside (IPTG) or the like may be added. When a microorganism transformed with an expression vector using trp promoter is cultured, indoleacetic acid (IAA) or the like may be added.

As a medium to culture a transformant obtained from an animal cell as a host, commonly used RPMI1640 medium or DMEM medium, or one of these media supplemented with fetal bovine serum, etc. may be used.

Usually, the cultivation is carried out in the presence 5% $CO_2$ at 37° C. for 1 to 30 days. During the cultivation, an antibiotic such as kanamycin or penicillin may be added to the medium if necessary.

After the cultivation, ZIC3 protein of the invention is extracted by disrupting the microorganisms or cells if the protein is retained within the microorganisms or cells. If ZIC3 protein of the invention is secreted outside of the microorganisms or cells, the culture fluid is used as it is or subjected to centrifugation to remove the microorganisms or cells. Thereafter, the resultant supernatant is subjected to conventional biochemical techniques used for isolating/purifying a protein. These techniques include ammonium sulfate precipitation, gel chromatography, ion exchange chromatography and affinity chromatography. These techniques may be used independently or in an appropriate combination to thereby isolate and purify ZIC3 protein of the invention from the above culture.

5. Antibody against the Protein of the Invention

In the present invention, antibody against ZIC3 protein of the invention can also be prepared. The term "antibody" means an antibody molecule as a whole which can bind to the peptide of the invention that is an antigen, or a fragment thereof (e.g. Fab or F(ab')$_2$ fragment). The antibody may be either polyclonal or monoclonal.

The antibody of the invention may be prepared by various methods. Such methods of antibody preparation are well known in the art [see, for example, Sambrook, J. et al., Molecular Cloning, Cold Spring Harbor Laboratory Press (1989)].

(1) Preparation of a Polyclonal Antibody against the Protein of the Invention

ZIC3 protein of the invention genetically engineered as described above or a fragment thereof is administered as an antigen to a mammal such as rat, mouse or rabbit. The dosage of the antigen administered per animal is 0.1 to 10 mg when no adjuvant is used, and 1 to 100 µg when an adjuvant is used. As an adjuvant, Freund's complete adjuvant (FCA), Freund's incomplete adjuvant (FIA), aluminium hydroxide adjuvant or the like may be enumerated. Immunization is performed mainly by intravenous, subcutaneous or intraperitoneal injection. The interval of immunization is not particularly limited; immunization is carried out one to 10 times, preferably 2 to 5 times, at intervals of several days to several weeks, preferably at intervals of 2 to 5 weeks. Subsequently, 6 to 60 days after the final immunization, antibody titer is determined by, preferably, enzyme immunoassay (EIA), radioimmunoassay (RIA) or the like. Blood is collected from the animal on the day when the maximum antibody titer is shown to thereby obtain antiserum. When purification of an antibody from the antiserum is necessary, the antibody can be purified by appropriately selecting a conventional method such as ammonium sulfate salting out, ion exchange chromatography, gel filtration, affinity chromatography, or using these methods in combination.

(2) Preparation of a Monoclonal Antibody against the Protein of the Invention (i) Recovery of Antibody-Producing Cells ZIC3 protein of the invention genetically engineered as described above or a fragment thereof is administered as an antigen to a mammal such as rat, mouse or rabbit. The dosage of the antigen administered per animal is 0.1 to 10 mg when no adjuvant is used, and 1 to 100 µg when an adjuvant is used. As an adjuvant, Freund's complete adjuvant (FCA), Freund's incomplete adjuvant (FIA), aluminium hydroxide adjuvant or the like may be enumerated. Immunization is performed mainly by intravenous, subcutaneous or intraperitoneal injection. The interval of immunization is not particularly limited; immunization is carried out one to 10 times, preferably 2 to 5 times, at intervals of several days to several weeks, preferably at intervals of 2 to 5 weeks. Subsequently, 1 to 10 days, preferably 3 days after the final immunization, antibody-producing cells are collected. As antibody-producing cells, spleen cells, lymph node cells, peripheral blood cells, etc. may be enumerated. Among them, spleen cells and local lymph node cells are preferable.

(ii) Cell Fusion

In order to obtain hybridomas, cell fusion between antibody-producing cells and myeloma cells is performed. As the myeloma cells to be fused to the antibody-producing cells, a commonly available cell strain of an animal such as mouse may be used. Preferably, a cell strain to be used for this purpose is one which has drug selectivity, cannot survive in HAT selective medium (containing hypoxanthine, aminopterin and thymidine) when unfused, and can survive there only when fused to antibody-producing cells. As myeloma cells, mouse myeloma cell strains such as P3X63-Ag.8.U1(P3U1), Sp2/0, NS-1 may be enumerated.

Subsequently, the myeloma cells and the antibody-producing cells described above are subjected to cell fusion. Briefly, $1 \times 10^9$ cells/ml of the antibody-producing cells and $1 \times 10^8$ cells/ml of the myeloma cells are mixed together in equal volumes in an animal cell culture medium such as serum-free DMEM or RPMI-1640, and reacted in the presence of a cell fusion promoting agent. As the cell fusion promoting agent, polyethylene glycol with an average molecular weight of 1,500 Da may be used, for example. Alternatively, the antibody-producing cells and the myeloma cells may be fused in a commercial cell fusion apparatus utilizing electric stimulation (e.g. electroporation).

(iii) Selection and Cloning of a Hybridoma

A hybridoma of interest is selected from the cells after the cell fusion. As a method for this selection, the resultant cell suspension is appropriately diluted with fetal bovine serum-containing RPMI-1640 medium or the like and then plated on microtiter plates at a density of about $2 \times 10^5$ cells/well. A selective medium is added to each well. Then, the cells are cultured while appropriately exchanging the selective medium. As a result, about 14 days after the start of cultivation in the selective medium, the growing cells can be obtained as hybridomas.

Subsequently, screening is performed as to whether the antibody of interest is present in the culture supernatant of the grown hybridomas. The screening of hybridomas may be performed by any of conventional methods. For example, a part of the culture supernatant of a well in which a hybridoma is grown is collected and subjected to enzyme immunoassay or radioimmunoassay.

Cloning of the fused cell is performed by the limiting dilution method or the like. Finally, the hybridoma of interest which is a monoclonal antibody producing cell is established.

(iv) Recovery of the Monoclonal Antibody

As a method for recovering the monoclonal antibody from the thus established hybridoma, conventional cell culture methods or the abdominal dropsy formation method may be employed.

In the cell culture method, the hybridoma is cultured in an animal cell culture medium such as 10% fetal bovine serum-containing RPMI-1640 medium, MEM medium or a serum-free medium under conventional culture conditions (e.g. at 37° C. under 5% $CO_2$) for 2 to 10 days. Then, the monoclonal antibody is recovered from the culture supernatant.

In the abdominal dropsy formation method, about $1 \times 10^7$ cells of the hybridoma is administered into the abdominal cavity of an animal syngeneic to the mammal from which the myeloma cells were derived, to thereby propagate the hybridoma greatly. One to two weeks thereafter, the abdominal dropsy or serum is collected.

In the above-mentioned method of recovery of the antibody, if purification of the antibody is necessary, the antibody can be purified by appropriately selecting a conventional method such as ammonium sulfate salting out, ion exchange chromatography, gel filtration, affinity chromatography, or using these methods in combination.

Once the polyclonal or monoclonal antibody is thus obtained, the antibody is bound to a solid carrier as a ligand to thereby prepare an affinity chromatography column. With this column, the peptide of the invention can be purified from the above-mentioned source or other sources. Besides, these antibodies can also be used in Western blotting to detect the protein of the invention.

6. Therapeutic Agent and Agent for Gene Therapy for Nervous Diseases

Since the protein and the gene of the invention has neurogenesis inducing activity, they are useful as a therapeutic agent and as an agent for gene therapy, respectively, for diseases of the nervous system. The therapeutic agent or the agent for gene therapy of the invention can be administered orally or parenterally and systemically or locally.

When the protein or the gene of the invention is used as a therapeutic agent or an agent for gene therapy for diseases of the nervous system, the disease to be treated is not particularly limited. For example, the protein or the gene may be used for Alzheimer's disease, amyotrophic lateral sclerosis, spinocerebellar degeneration, Parkinson's disease, cerebral ischemia or the like for the specific purpose of treatment or prevention. These diseases may be in the form of a single disease or may be complicated by one of these diseases or by some disease other than those mentioned above; any of such forms may be treated with the protein or the gene of the invention.

When the therapeutic agent of the invention is administered orally, the agent may be formulated into a tablet, capsule, granule, powder, pill, troche, internal liquid agent, suspension, emulsion, syrup or the like. Alternatively, the therapeutic agent may be prepared into a dry product which is re-dissolved just before use. When the therapeutic agent of the invention is administered parenterally, the agent may be formulated into a intravenous injection (including drops), intramuscular injection, intraperitoneal injection, subcutaneous injection, suppository, or the like. Injections are supplied in the form of unit dosage ampules or multi-dosage containers.

These formulations may be prepared by conventional methods using appropriate excipients, fillers, binders, wetting agents, disintegrating agents, lubricating agents, surfactants, dispersants, buffers, preservatives, dissolution aids, antiseptics, flavoring/perfuming agents, analgesics, stabilizers, isotonicity inducing agents, etc. conventionally used in pharmaceutical preparations.

Each of the above-described formulations may contain pharmaceutically acceptable carriers or additives. Specific examples of such carriers or additives include water, pharmaceutically acceptable organic solvents, collagen, polyvinyl alcohol, polyvinylpyrrolidone, carboxyvinyl polymers, sodium alginate, water-soluble dextran, sodium carboxymethyl amylose, pectin, xanthan gum, gum arabic, casein, gelatin, agar, glycerol, propylene glycol, polyethylene glycol, vaseline, paraffin, stearyl alcohol, stearic acid, human serum albumin, mannitol, sorbitol and lactose. One or a plurality of these additives are selected or combined appropriately depending on the form of the preparation.

The dosage levels of the therapeutic agent of the invention will vary depending on the age of the subject, the route of administration and the number of times of administration and may be varied in a wide range. When an effective amount of the protein of the invention is administered in combination with an appropriate diluent and a pharmaceutically acceptable carrier, the effective amount of the protein can be in the range from 0.01 to 1000 mg/kg per administration. The therapeutic agent is administered once a day or in several dosages per day for at least one day.

When the gene of the invention is used as an agent for gene therapy for diseases of the nervous system, the gene of the invention may be directly administered by injection. Alternatively, a vector incorporating the gene of the invention may be administered. Specific examples of a suitable vector for this purpose include an adenovirus vector, adeno-associated virus vector, herpes virus vector, vaccinia virus vector and retrovirus vector. The gene of the invention can be administered efficiently by using such a virus vector. Alternatively, the gene of the invention may be enclosed in phospholipid vesicles such as liposomes, and the resultant liposomes may be administered to the subject. Briefly, since liposomes are biodegradable material-containing closed vesicles, the gene of the invention is retained in the internal aqueous layer and the lipid bilayer of liposomes by mixing the gene with the liposomes (a liposome-gene complex). Subsequently, when this complex is cultured with cells, the gene in the complex is taken into the cells (lipofection). Then, the resultant cells may be administered by the methods described below.

As a method for administering the agent for gene therapy of the invention, local administration to tissues of the central nervous system (brain, spiral cord) may be performed in addition to conventional systemic administration such as intravenous or intra-arterial administration. Further, an administration method combined with catheter techniques and surgical operations may also be employed.

The dosage levels of the agent for gene therapy of the invention vary depending on the age, sex and conditions of the subject, the route of administration, the number of times of administration, and the type of the formulation. Usually, it is appropriate to administer the gene of the invention in an amount of 0.1–100 mg/adult body/day.

According to the present invention, there are provided a neurogenesis inducing protein; a neurogenesis inducing gene zic3 coding for the protein; a recombinant vector comprising the gene; a transformant comprising the vector; an antibody against the above protein; and a therapeutic agent for nervous diseases. The Zic3 gene of the invention is useful as a diagnostic agent for diseases of the nervous system, a therapeutic agent for Alzheimer's disease and the like, and a probe to detect diseases of the nervous system.

EXAMPLES

Hereinbelow, the present invention will be described more specifically with reference to the following Examples. However, the technical scope of the present invention is not limited to these Examples.

Example 1

Cloning of the Zic3 Gene (1) Preparation of Poly(A+) RNA from *Xenopus laevis* Neurula Eggs of *Xenopus laevis* (Hamamatsu Seibutsu Kyozai, Shizuoka Pref.) were incubated artificially according to the method of Newport [Newport, Cell 30:675–686 (1982)] to obtain embryos. The embryo was dipped in 2% cysteine-HCl (pH 7.8) to remove the jelly coat and then cultured in 0.1×Steinberg's solution (60 mM NaCl, 0.67 mM KCl, 0.34 mM Ca(NO$_3$)$_2$, 0.83 mM MgSO$_4$, 10 mM Hepes, pH 7.4), followed by recovery of the neurula.

From the recovered neurula, total RNA was extracted according to AGPC method. Subsequently, poly(A+) RNA was separated and purified therefrom using Oligotex dT30 (Roche).

(2) Preparation of a cDNA Library cDNA was synthesized using the poly(A+) RNA from (1) above and Time Saver™ cDNA Synthesis Kit (Pharmacia). Briefly, single-stranded cDNA fragments were synthesized using the poly(A+) RNA as a template, oligo(dT)$_{12-18}$ primers and a cloned mouse reverse transcriptase. Then, double-stranded cDNA fragments were synthesized using *E. coli* RNase H and *E. coli* DNA polymerase.

The resultant double-stranded cDNA fragments were blunt-ended using Klenow fragment (Nippon Gene). Thereafter, an adaptor having an EcoRI restriction site at one end and a blunt end at the other end was ligated to the cDNA fragments using T4 DNA ligase. After phosphorylation of the EcoRI restriction site with T4 polynucleotide kinase, the cDNA fragments were introduced into the EcoRI site in the multicloning site of λ ZAP II (a phage cloning vector) using a commercial kit (ZAP II™ Vector Kit; Stratagene). Thus, the packaging of cDNA was performed. Subsequently, the resultant phage vector was transformed into *E. coli* XLI-Blue, a host, to thereby prepare a cDNA library.

(3) Preparation of Primers Specific to the Amino Acid Sequence of the Zinc Finger Motif of the Zic Gene Family Primers were synthesized based on well conserved amino acid sequences in the mouse zinc finger domain. Briefly, as 5' primer, 5'-GAGAACCTCAAGATCCACAA-3' (SEQ ID NO: 5) was synthesized based on Glu Asn Leu Lys Ile His Lys (SEQ ID NO: 3). As 3' primer, 5'-TT(C/T)CCATG(A/G)ACCTTCATGTG-3' (SEQ ID NO: 6) was synthesized based on His Met Lys Val His Glu Glu (SEQ ID NO: 4).

The synthetic oligonucleotides were chemically synthesized with an automated synthesizer (Applied Biosystem).

(4) Preparation of a cDNA Probe for Clone Isolation by PCR

A PCR was performed using the cDNA from (2) above as a template and the 5' and 3' primers from (3) above. The composition of the PCR reaction solution was as follows.

| | |
|---|---|
| First strand cDNA solution | 1 µl |
| Sterilized water | 70 µl |
| 10x PCR buffer | 10 µl |
| 25 mM MgCl$_2$ | 6 µl |
| 2 mM dNTP mix | 10 µl |
| 100 µM 5' primer (sense) | 1 µl |
| 100 µM 3' primer (antisense) | 1 µl |
| 5 U/µl Taq polymerase | 1 µl |

After the above reaction solution was thoroughly mixed, 50 µl of mineral oil was layered over the solution. A PCR was performed in a DNA thermal cycler for 30 cycles, one cycle consisting of reaction at 94° C. for 1 min, at 55° C. for 1 min and at 74° C. for 2 min. As a result, a fragment of 208 bp was obtained. This fragment was labelled with α-$^{32}$P-dCTP using a random primer labeling kit (Takara) to obtain a cDNA probe for clone isolation.

(5) Isolation of a Clone

The cDNA library obtained in (2) above was plated on 12 NYZ plates (Falcon) so that ca. 150,000 plaques would be formed per plate. Upon this plate, a nylon filter Colony/Plaque Screen (Dupont NEN) was placed and fixed with 0.5 N NaOH aqueous solution. Then, hybridization was performed in a hybridization buffer (50% formamide, 1 M NaCl, 10% dextran sulfate, 1% sodium dodecyl sulfate, 100 µg/ml denatured salmon sperm DNA) containing the labelled probe from (4) above at 42° C. for 18 hours.

One clone was obtained from this screening. XL1-Blue was co-infected with the resultant clone and a helper phage R408 (Stratagene) to thereby cut out the cDNA insert from λZAP II to pBluescriptSK(-), which was then transformed into XL1-Blue. As a result, one clone having an insert of ca. 2.4 kb was obtained.

(6) Determination of the cDNA Nucleotide Sequence

The nucleotide sequence of the clone obtained in (5) above was analyzed using ABI PRISM™ Dye Cycle Ready Reaction Kit (Perkin-Elmer) and a fluorescent automated DNA sequencer (Applied Biosystems). As a result, the nucleotide sequence for the Zic3 gene with a length of 2364 bases was obtained (SEQ ID NO: 1). This cDNA had a deduced amino acid sequence consisting of 441 amino acids (SEQ ID NO: 2).

A homology search was performed against GenBank/EMBL nucleic acid databases using FASTA homology search program [Pearson et al., Proc. Natl. Acad. Sci. USA 85: 2444–2448 (1988)]. As a result, the nucleotide sequence of the gene of the invention exhibited 76% homology to that of mouse Zic3 gene [Aruga, J. et al., J. Biol. Chem. 271: 1043–1047 (1996)]. With respect to the amino acid sequence, the gene of the invention exhibited 66% and 35% homology to other Zic [Aruga, J. et al., J. Biol. Chem. 271: 1043–1047 (1996)] and Opa [Benedyk et al, Genes Dev. 8: 105–117 (1994)], respectively. Accordingly, the gene of the invention was designated Xenopus Zic3 (also called the "Zic3 gene" or "Zic3").

Example 2
Functions of the Zic3 Gene of the Invention (1) Analysis of the Expression Pattern of Zic3 in Xenopus Embryos In order to elucidate the expression pattern of the Zic3 gene of the invention in Xenopus embryos, whole mount in situ hybridizations were performed [Shain and Zuber, J. Biochem. Biophys. Methods 31: 185–188 (1996)].

A digoxigenin (DIG)-labelled RNA probe for hybridization was synthesized according to the method of Harland [Harland, R. M., Methods in Cell Biology 36: 685–694 (1991)]. Briefly, RNA was synthesized from 2.5 μg of the cDNA clone containing the Zic3 gene obtained in Example 1 using RNA polymerase, followed by DIG labelling. After the resultant DIG-labelled RNA probe was treated with DNase, sodium acetate solution was added thereto to give a final concentration of 0.5 M and then the probe was ethanol-precipitated with 3 volumes of ethanol. The resultant mixture was micro-centrifuged for 5 min at 12,000 rpm to precipitate the probe, which was re-suspended in 20 μl of 80% formamide and stored at −20° C.

On the other hand, Xenopus embryos cultured up to individual stages in the same manner as described in section (1) in Example 1 were fixed with a formalin fixative and stored in methanol at −20° C. For the purpose of in situ hybridization, the embryos were distributed into 5 ml screw vials. The vial was shaken on Nutator (Becton-Dickinson) at room temperature.

The embryo was dipped in 50% methanol/50% 0.1 M triethanolamine (TEA, pH 7.5) for 5 min and then washed with TEA for 5 min. The embryo was incubated for 10 min in a mixture of TFA and acetic anhydride mixed at a ratio of 1 ml:5 μl. Subsequently, the embryo was dipped in a mixed solution of TEA and 3.7% formaldehyde for fixation. Prehybridization was performed by adding thereto a prehybridization solution (50% formamide, 5xSSPE, 5% SDS, 1 mg/ml Torula RNA) and allowing it to stand at 60° C. for 1 hr and 10 min. Then, the prehybridization solution was replaced with a sufficient amount of a hybridization solution (obtained by adding the DIG-labelled RNA probe to the prehybridization solution at 1 μg/ml). An overnight incubation was performed at 60° C. for hybridization.

After the hybridization, the embryo was washed twice with 2xSSC containing 50% formamide at 60° C. for 30 min each time. Subsequently, the embryo was rinsed with maleate buffer (MAB; 100 mM maleic acid, 150 mM NaCl, pH 7.5) for 5 min and then blocked with MAB containing 2% BMB (Boehringer-Mannheim Blocking Reagent) for 1 hr. The embryo was further incubated in MAB containing 2% BMB and 20% thermally treated sheep serum for 1 hr. Then, anti-dioxigenin antibody-conjugated alkaline phosphatase (Boehringer-Mannheim) was added thereto at 0.5 μl/ml, and incubation was continued for another 4 hr at room temperature. The resultant embryo was washed with MAB for 1 hr at least 5 times, and then dipped in alkaline phosphatase buffer (100 mM Tris, 50 mM $MgCl_2$, 100 mM NaCl, pH 9.5) for 10 min at room temperature for equilibration.

Per ml of the above buffer, 4.5 μl of nitroblue tetrazolium solution (NTB; 75 mg/ml of 70% dimethylformamide) and 3.5 μl of 5-bromo-4-chloro-3-indolylphosphoric acid (BCIP; 50 mg/ml of dimethylformamide) were added. The resultant mixture was incubated to induce the coloring reaction. The coloring was terminated by adding TE (10 mM Tris-HCl, 1 mM EDTA, pH 8.0). Re-fixing and mounting were carried out according to the method of Harland [Harland, R. M., Methods in Cell Biology 36: 685–694 (1991)].

As a result, Zic3 expression was detected at early gastrula in the dorsal lip and in the prospective neural plate [FIG. 1A (stage 10.25) and B (stage 10.5)]. In FIG. 1, an arrow indicates the gastrula and arrowheads indicate the prospective neural plate.

As gastrulation proceeded, expression of the Zic3 gene of the invention decreased in the dorsal lip and increased in the prospective neural plate [FIG. 1B and C (stage 10.5)]. FIG. 1C shows a cross section of the embryo shown in FIG. 1B.

In late gastrula, Zic3 expression diminished gradually in the central region (FIG. 1D, stage 12). At the neural plate stage (FIG. 1E, stage 14), Zic3 was expressed strongly in the prospective regions of mesencephalon and anterior rhombencephalon. Thereafter, Zic3 expression became stronger in the anterior neural holds, whereas that in the trunk neural folds remained weak (FIG. 1F, stage 16).

At early tailbud stage (FIG. 1G and H, stage 20), Zic3 expression became gradually restricted to the dorsal region of the forebrain (telencephalon and diencephalon), the midbrain and the hindbrain, and its expression was weak in the dorsal region of the trunk.

After mid-tailbud stage, Zic3 expression disappeared in the diencephalon, but additional expression could be definitely confirmed in the lateral mesoderm of the tailbud region (FIG. 1I, stage 30). The cross section through the head at stage 30 showed that Zic3 expression was restricted to the dorsal part of the neural tube (FIG. 1J). In FIG. 1J, "nt" represents the neural tube; "ne" represents eyes; "fg" represents fore-gut.

From these results, it was found that Zic3 is expressed in those regions which are closely related to early neurogenesis.

(2) RT-PCR Analysis of the Temporal Expression Profiles of zic3 and Various Neural Marker Genes Because Zic3 is expressed in the prospective neural plate region during gastrulation, the inventors compared the temporal expression profile of Zic3 with those of other neural marker genes.

The marker genes used in this experiment were genes coding for NCAM, N-tubulin and transcription factors XASH-3, XATH-3, XlPOU2 and NeuroD [Lee, J. E. et al., Science 268: 836–844 (1995); Ferreiro, B. et al., Development 120: 3649–3655 (1994); Turner and Weintraub, Genes Dev. 8:1434–1447 (1994); Takebayashi, K. et al., EMBO J. 16:384–395 (1997); Witta, S. E. et al., Development 121: 721–730 (1995); Chitnis, A. et al., Nature 375: 761–766 (1995); Kintner and Melton, Development 99: 321–325 (1987); Zimmerman, K. et al., Development 119: 221–231 (1993); Oschwald, R. et al., Int. J. Dev. Biol. 35: 399–405 (1991)].

These genes can be obtained by synthesizing primers from the nucleotide sequence of the relevant gene described in the above references, using genomic DNA from Xenopus or the like as a template and utilizing PCR techniques known in the art to amplify the relevant gene.

Comparison of temporal expression profiles was performed by RT-PCR. Briefly, total RNA was extracted separately from embryos at the individual stages of egg, 8-cell, morula, blastula, gastrula, neurula and tailbud, and subjected to RT-PCR. As an indicator for RNA recovery ratio, Histone H4 was used [Turner and Woodland, nucleic Acids Res. 10:3769–3780 (1980)]. As a positive control, sibling control embryos were used. As a control to check the absence of genomic DNA, a PCR was performed without reverse transcription.

Specifically, each embryo of the above-indicated stage was suspended in 100 µl of a denaturing solution (4 M guanidine thiocyanate, 25 mM sodium citrate, 0.1 M 2-mercaptoethanol, 0.5% N-lauroyl sodium sarcosine) in a 1.5 ml microtube and shaken vigorously. To this suspension, 10 µl of 2 M sodium acetate (pH 4.0) was added and mixed thoroughly. Subsequently, 100 µl of water-saturated phenol was added thereto and mixed. Then, 30 µl of CIA (chloroform:isoamyl alcohol=49:1 by volume) and 1 µl of Etachinmate (Nippon Gene) were added to the mixture and shaken vigorously. The resultant mixture was left stationary on ice for 15 min. After centrifugation at 4° C. at 15,000 rpm for 20 min, the resultant upper layer was recovered into a fresh tube. Then, 250 µl of ethanol was added to the tube, which was centrifuged at 4° C. at 15,000 rpm for 10 min to thereby pellet the RNA. The supernatant was discarded, and the tube was air-dried. Then, 88 µl of sterilized water, 10 µl of 10×DNase buffer (BRL), 1 µl of RNasin (Promega), and 1 µl of DnaseI (Takara) were added to the tube and reacted at 37° C. for 1 hr to thereby degrade the DNAs mixed therein.

Subsequently, 100 µl of ethanol was added to the tube, which was centrifuged at 4° C. at 15,000 rpm for 10 min to thereby pellet the RNA.

The supernatant was discarded. After the tube was air-dried, 100 µl of solution K (0.01 M Tris, 0.005 M EDTA, 0.5% SDS, pH 7.8) and 1 µl of 20 mg/ml proteinase K solution were added to the tube and reacted at 37° C. for 1 hr to thereby degrade the proteins mixed therein. Then, 100 µl of phenol/CIA were added to the tube and mixed. The resultant mixture was centrifuged at 4° C. at 15,000 rpm for 10 min. Thereafter, 100 µl of CIA was added further and mixed. The resultant mixture was centrifuged at 4° C. at 15,000 rpm for 10 min. The resultant upper layer was recovered into a fresh tube, to which 250 µl of ethanol was added. Then, the tube was centrifuged at 4° C. at 15,000 rpm for 10 min to thereby pellet the RNA. The supernatant was discarded. The tube was air-dried and then allowed standing at room temperature.

The resultant RNA sample was dissolved in 10 µl of DEPC-treated water (obtained by adding 0.2 ml of diethylpyrocarbonate to 100 ml of distilled water, shaking the mixture vigorously and autoclaving it), and 3 µl of this solution was placed into a microtube. To the microtube, 1 µl of 100 pmol/µl random hexamer (Takara) and 7 µl of sterilized water were added and mixed thoroughly. The resultant mixture was incubated at 72° C. for 2 min and at 37° C. for 5 min. Subsequently, 4 µl of 5× RT buffer, 0.1 M DTT, 2 µl of 5 mm DNTP mix, and 0.5 µl of mouse leukemia virus (MMLV)-derived reverse transcriptase (BRL) were added thereto and mixed thoroughly. Then, a reverse transcription reaction was performed at 37° C. for 1 hr. Subsequently, the reaction solution was maintained at 98° C. for 10 min to terminate the reaction. Thus, a solution of the first strand cDNA was obtained and stored at −20° C. until use for the PCR synthesis of the second strand.

A PCR was performed using the first strand cDNA solution obtained above as a template. The composition of the PCR reaction solution was as follows.

| | |
|---|---|
| First strand cDNA solution | 1 µl |
| Sterilized water | 70 µl |
| 10× PCR buffer | 10 µl |
| 25 mM MgCl$_2$ | 6 µl |
| 2 mM dNTP mix | 10 µl |
| 100 µM primer (sense) | 1 µl |
| 100 µM primer (antisense) | 1 µl |
| 5 U/µl Taq polymerase | 1 µl |

After the above reaction solution was mixed thoroughly, 50 µl of mineral oil was layered over the solution. A PCR was performed 25–36 cycles, one cycle consisting of thermal. denaturation at 94° C. for 0.5 min, annealing at 55° C. for 0.5 min and extension at 72° C. for 1 min. After completion of the reaction, 4 µl of the reaction solution was subjected to agarose gel electrophoresis to examine the amplified product. Thus, expression of each gene was investigated.

| | | | |
|---|---|---|---|
| Zic3 | (sense) | 5'-TTCTCAGGATCTGAACACAT-3' | (SEQ ID NO: 7) |
| | (antisense) | 5'-CCCTATAAGACAAGGAATAC-3' | (SEQ ID NO: 8) |
| XASH-3 | (sense) | 5'-GGACTCTCGCCTTGTGGC-3' | (SEQ ID NO: 9) |
| | (antisense) | 5'-GATATGTTCTTGTAATAGTCAGT-3' | (SEQ ID NO:10) |
| XATH-3 | (sense) | 5'-TGGACCTCAGGCCATGTTC-3' | (SEQ ID NO:11) |
| | (antisense) | 5'-GATGCTGAGTGGAGGTGTTA-3' | (SEQ ID NO:12) |
| X1POU 2 | (sense) | 5'-ACCCAACGACCACGTGGACCTG-3' | (SEQ ID NO:13) |
| | (antisense) | 5'-AGCTCATTGCAGGAGGTGTCTG-3' | (SEQ ID NO:14) |
| NeuroD | (sense) | 5'-GTGAAATCCCAATAGACACC-3' | (SEQ ID NO:15) |
| | (antisense) | 5'-TTCCCCATATCTAAAGGCAG-3' | (SEQ ID NO:16) |
| NCAM | (sense) | 5'-CACAGTTCCACCAAATGC-3' | (SEQ ID NO:17) |
| | (antisense) | 5'-GGAATCAAGCGGTACAGA-3' | (SEQ ID NO:18) |

```
                    -continued
N-tubulin      (sense)     5'-ACACGGCATTGATCCTACAG-3'       (SEQ ID NO:19)

(antisense) 5'-AGCTCCTTCGGTGTAATGAC-3'       (SEQ ID NO:20)

Histone H4     (sense)     5'-CGGGATAACATTCAGGGTATCACT-3'   (SEQ ID NO:21)

(antisense) 5'-ATCCATGGCGGTAACTGTCTTCCT-3'   (SEQ ID NO:22)
```

Figure 2:
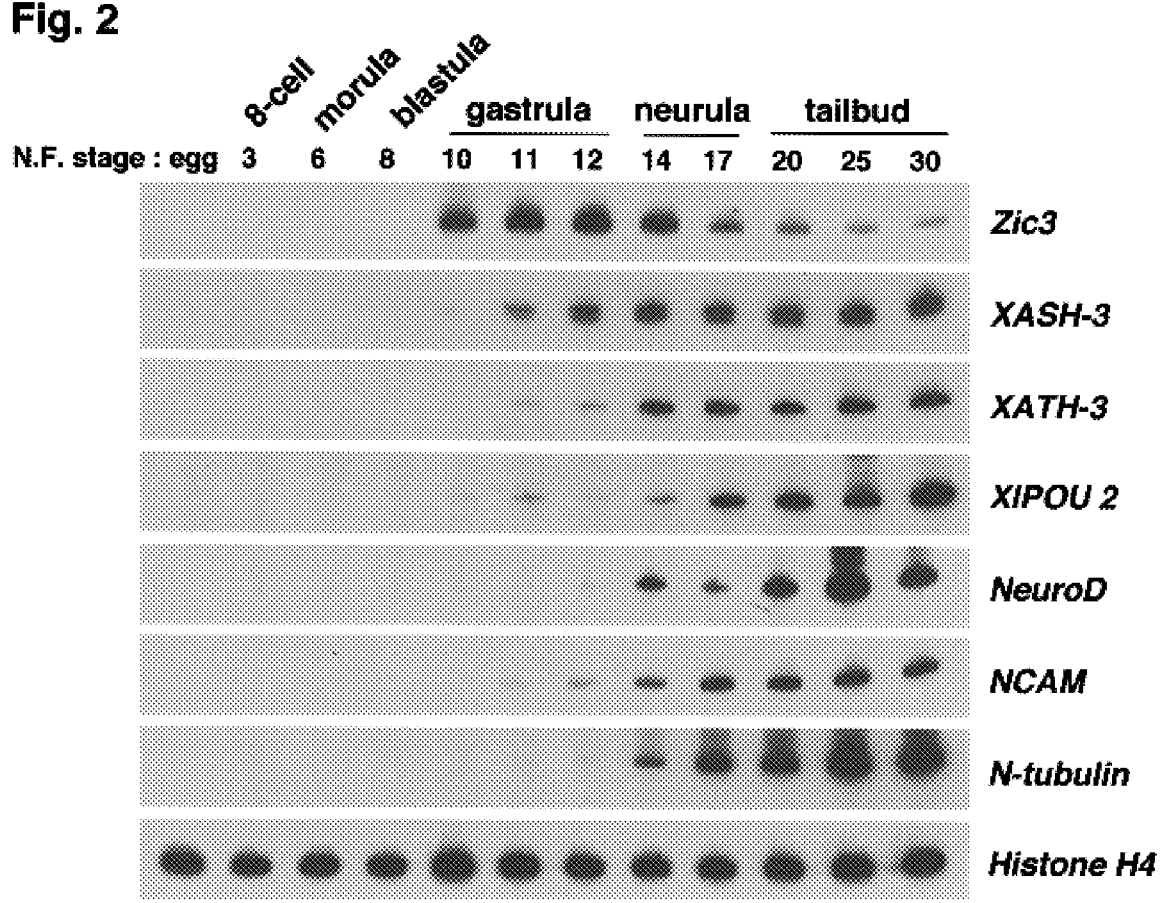
FIG. 2 presents autoradiographs showing the results of expression analysis of the Zic3 gene.

The results are shown in FIG. 2. As is clear from FIG. 2, Zic3 expression was detected in early gastrula (stage 10). With respect to the expression of other neural marker genes, XATH-3 and NCAM were detected at mid-gastrula stage; and NeuroD and N-tubulin were detected at late gastrula stage. Although XASH-3 and XlPOU 2 were detected also at early gastrula stage, their expression was extremely weak compared to Zic3 expression.

Zic3 was first detected in the prospective neural plate region immediately after neural induction (FIG. 1A). Therefore, the inventors compared precisely the onset of expression of Zic3 and a neural inducer gene chordin which is known to be expressed at an early stage of neurogenesis [Sasai, Y. et al., Cell 79:779–790 (1994)]. This comparison was made with the following techniques.

Xenopus eggs were artificially fertilized with sperms in a culture plate, and the embryonic development of all the fertilized eggs was allowed to proceed in a synchronized manner. After the artificial fertilization, the eggs were cultured at 23° C. for 6 to 10.5 hr. Then, embryos were collected and immediately frozen. Zic3 RNA was extracted from these samples in the same manner as described in Section (1), Example 1, and subjected to an RT-PCR. For chordin, an RT-PCR was performed using the following primers.

```
Chordin    (sense)     5'-AACTGCCAGGACTGGATGGT-   (SEQ ID NO:23)
                          3'

(antisense) 3'-GGCAGGATTTAGAGTTGCTTC-  (SEQ ID NO:24)
                          3'
```

Figure 3:
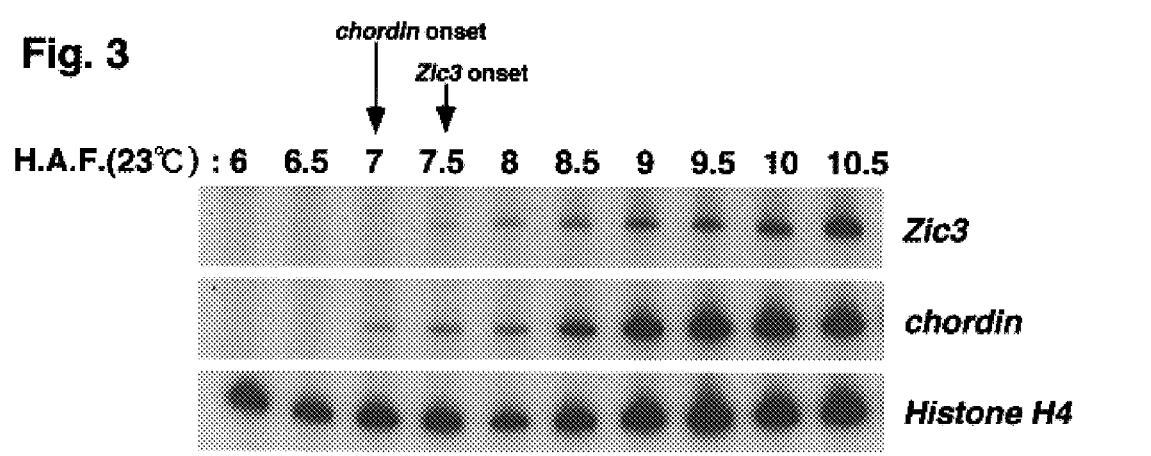
FIG. 3 presents autoradiographs showing the results of expression analysis of the Zic3 gene.

As a result, it was found that the onset of Zic3 expression is 7.5 hr after the fertilization, whereas that of chordin is 7 hr after the fertilization (FIG. 3). The numbers indicated above the lanes represent hours of cultivation after the artificial fertilization. Since the onset of Zic3 expression is only 30 min later than that of chordin, it was found that, like chordin, Zic3 also induces the initial step of neural induction.

(3) Zic3 Expression Inducing Mechanism

The ectoderm (animal cap) of Xenopus laevis oocyte can be neuralized by prolonged culture in dispersal [Grunz, H. et al., Cell Differ. Dev. 28:211–218 (1989); Godsave, S. F. et al., Dev. Biol. 134:486–490 (1989)]. This occurs because ectoderm cells are relieved from neuralization repressors as a result of dispersion of the cells.

Then, the inventors examined whether Zic3 is induced in animal cap explants.

Briefly, an animal cap explant was dipped in a buffer without $Ca^{2+}$ and $Mg^{2+}$ ions and pipetted lightly to thereby obtain dispersed cells. The cells were cultured under such condition in a medium without $Ca^{2+}$ and $Mg^{2+}$ ions at 23° C. for 4 hr. Then, the cells were allowed to form a cell mass again, and the mass was cultured up to a time point equivalent to the neurula stage.

Subsequently, the expression of Zic3 and other genes (epidermal keratin, NCAM, Xtwi, Xslu and Histone H4) was tested by RT-PCR. Briefly, RNA was extracted from non-dispersed animal cap explants and dispersed animal cap explants. As primers for individual genes, the above-mentioned primers and those described below were used. A series of RT-PCRs were performed under the same conditions as in Section (1) in this Example (animal cap assay)

```
Epidermal keratin   (sense)     5'-CACCAGAACACAGAGTAC-3'    (SEQ ID NO:25)

(antisense) 5'-CAACCTTCCCATCAACCA-3'    (SEQ ID NO:26)

Xtwi                (sense)     5'-AGTCCGATCTCAGTGAAGGGCA-3' (SEQ ID NO:27)

(antisense) 5'-TGTGTGTGGCCTGAGCTGTAG-3' (SEQ ID NO:28)

Xslu                (sense)     5'-GCCCTATTTCCTTGTTGC-3'    (SEQ ID NO:29)

(antisense) 5'-AACCCTTCTTGGTTGCAC-3'    (SEQ ID NO:30)
```

The results are shown in FIG. 4A. In each lane, "Intact" represents animal cap explants (non-dispersed cells); "Dispersed" represents animal caps cultured in dispersal; "Embryo" represents embryos; and "RT-" represents the results without reverse transcriptase. Zic3 expression was not detected in intact animal cap explants, though the expression of epidermal keratin (an epidermal marker gene) was detected. On the other hand, expression of Zic3 and a neural marker gene NCAM was detected in dispersed cells, but expression of epidermal keratin was not detected.

The neuralization that occurs in animal cap-derived dispersed cells is considered to be due to the attenuation of BMP4-mediated signals which induce ectodermal cells into epidermal cells [Wilson and Hemmati-Brivanlou, Nature 376:331–333 (1995)]. Therefore, the inventors performed the following experiment on the assumption that Zic3 expression can actually be induced in vivo by blocking the BMP4-mediated signals.

Briefly, a dominant negative form of BMP receptor (dnBMPR) mRNA [Suzuki, A. et al., Devlop. Growth. Differ. 37:581–588 (1995)] was injected into embryos to over-express dnBMPR therein. Then, Zic3 expression in early gastrula stage embryos was examined by in situ hybridization in the same manner as described above.

Specifically, Zic3 MRNA and dnBMPR MRNA were synthesized by in vitro transcription. Zic3 MRNA (100 pg) was injected into a two-cell stage embryo with a glass microneedle. As a control, LacZ mRNA-injected early gastrula was used. dnBMPR mRNA (500 pg) was injected into the ventral region of a two-cell stage embryo, which was developed in 1×Steinbergxs solution containing 5% Ficoll up to the early gastrula of stage 10.25. The resultant embryo was subjected to whole mount in situ hybridization which was performed in the same manner as described above to thereby examine Zic3 expression.

As a result, in both the dnBMPR mRNA-injected embryo and the dnBMPR mRNA non-injected embryo, Zic3 expression was observed at naturally expected sites (arrowheads, FIG. 4B). In the dnBMPR mRNA-injected embryo, expression of ectopic Zic3 was induced in the ventromarginal zone of the gastrula (arrows, FIG. 4B). This shows that injection of dnBMPR mRNA causes expression of excessive dnBMPR in cells, which in turn inhibits the BMP4 signals and induces the neuroectoderm [Zimmerman, L. B. et al., Cell 86:599–606 (1996)]. Thus, it was found that Zic3 expression can be induced in vivo by blocking the BMP4 signals.

(4) Zic3 Overexpression Test in Early Embryos

The expression pattern of Zic3 in Xenopus and its activity to regulate neural induction suggest that Zic3 plays some role in early steps of neurogenesis. Then, the inventors examined the function of Zic3 by overexpression analysis in embryos.

First, Zic3 MRNA was injected into one blastomere of two-cell stage embryos so that Zic3 would be overexpressed in the left or right hemilateral body alone.

Briefly, Zic3 mRNA, LacZ mRNA and dnBMPR MRNA were synthesized by in vitro transcription in the same manner as described above. Zic3 mRNA was injected into one blastomere of two-cell stage embryos or two blastomeres of eight-cell stage embryos independently or in combination with LacZ mRNA. dnBMPR mRNA (500 pg) was injected into the ventral region of two-cell stage embryos. For animal cap assay, Zic3 mRNA was injected into the animal hemisphere of the two blastomeres of two-cell stage embryos. As control, embryos injected with LacZ mRNA alone or $H_2O$ alone or non-injected embryos were also tested. Injected embryos were cultured in 1×Steinberg's solution containing 5% Ficoll until midblastula stage. Then, they were transferred into 0.1× Steinberg's solution and subjected to animal pole assay at stage 9 or in situ hybridization at various stages in the same manner as described above.

Figure 5:
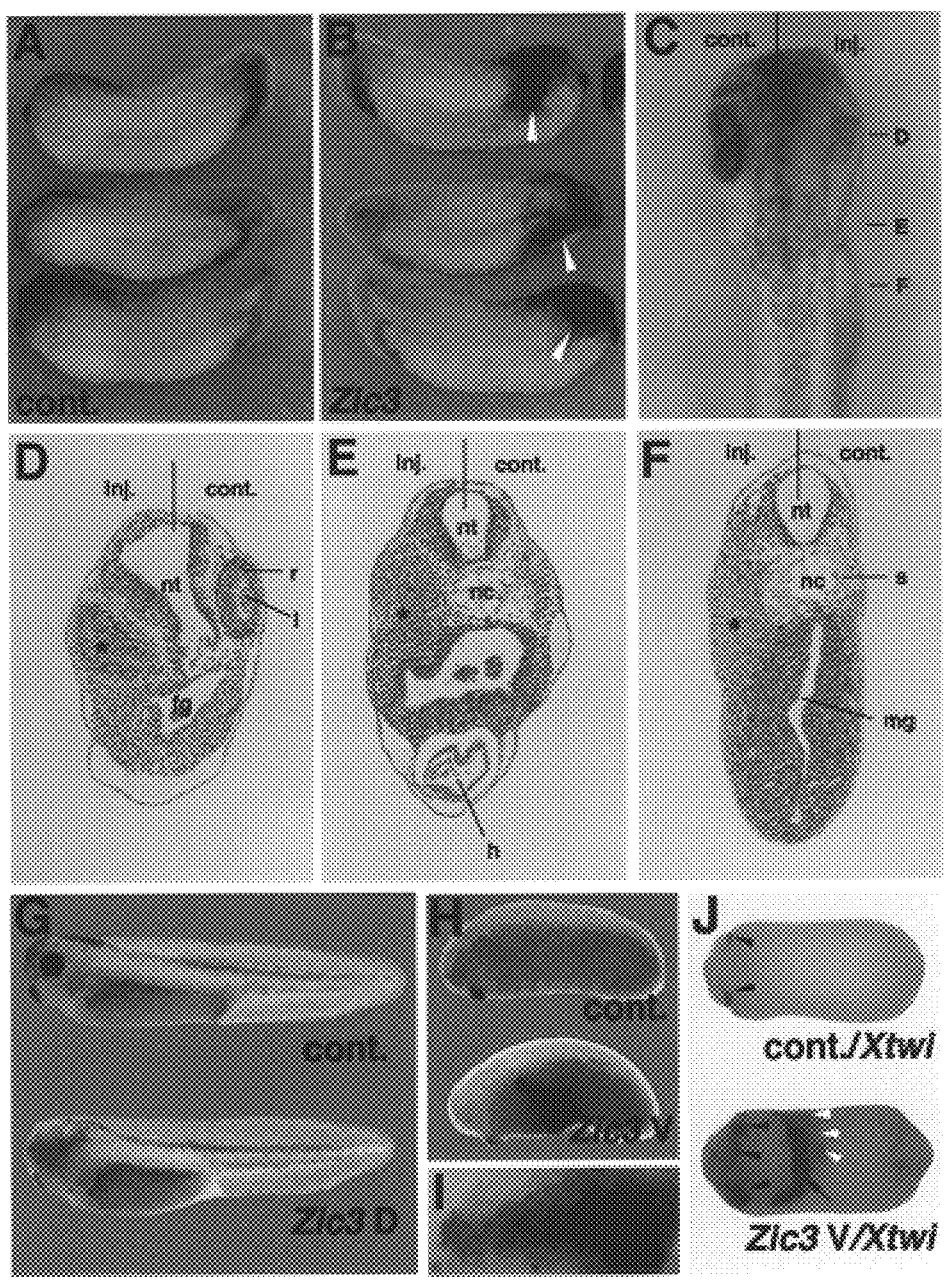
FIGS. 5A–5J present photographs showing the results of expression analysis of the Zic3 gene (morphology of an organism).

The results are shown in FIG. 5. In FIG. 5, panel A shows the Zic3 MRNA uninjected control side of the embryo (stage 27); panel B shows Zic3 mRNA injected side (stage 27). Panel C shows a dorsal view of the anterior region of Zic3 mRNA injected embryo (stage 36). Panels D-F are microscopic photographs of transverse sections of the embryo shown in panel C. Panels G-J show overexpression of .Zic3 when 100 pg of Zic3 mRNA or control LacZ mRNA was injected into two blastomeres of eight-cell stage embryos. In panel G (stage 36), mRNA was injected into two dorsoanimal blastomeres; in panels H–J (H, I: stage 25, J: stage 20), mRNA was injected into two ventroanimal blastomeres. In panels G and H, upper figures show lateral views of control LacZ mRNA injected embryos; and lower figures show lateral views of Zic3 mRNA injected embryos. Panel I shows higher magnification of the clusters in panel H. Panel J shows Xtwi expression in the embryos injected with LacZ mRNA or Zic3 mRNA into ventroanimal two blastomeres at eight-cell stage.

In almost all cases, the head side of the Zic3 mRNA injected embryos was enlarged and exhibiting poorly formed eyes (FIG. 5B, C), whereas Zic3 mRNA uninjected embryos exhibited normally formed eyes (FIG. 5A, C).

The sections through the head region of the Zic3 MrNA injected embryos showed that neural walls were considerably thickened in the injected side (FIGS. 5D–F). In addition to this change in neural walls, presumptive mesenchymal tissue, which may derive from the neural crest in the cephalic region, showed a remarkable hyperplasia. In most cases, however, neural retinas were considerably distorted and less hyperplastic (FIG. 5D). Besides, retinal pigment cells diminished and, in particular, lenses were not induced at all (FIG. 5C, D). Further, eye abnormalities were observed in the embryos injected with Zic3 mRNA into dorsal blastomeres (FIG. 5G, lower). Remarkable clusters of ectopic pigment cells appeared in the embryos injected with Zic3 mRNA into ventral blastomeres (FIG. 5H, lower). In contrast, no such abnormalities were observed in Zic3 mRNA uninjected embryos.

On the other hand, Xtwi expression was observed in the head neural crest of the control embryo (FIG. 5J, upper, arrowhead).

In contrast, expression of ectopic Xtwi was induced near the ectopic clusters of pigment cells in the ventral side of Zic3 mRNA injected embryos (FIG. 5J, lower, white arrowheads). The expansion of the Xtwi expressing cephalic neural crest (FIG. 5J, lower, black arrowheads) was observed in eight-cell stage embryos, and ectopic clusters of pigment cells were observed in the cephalic region (FIG. 5B).

Subsequently, the inventors injected Zic3 MRNA into two dorsoanimal or ventroanimal blastomeres of eight-cell stage embryos to express Zic3 restrictedly at the dorsal or ventral side (FIG. 5G–J). This experiment was performed in the same manner as described above using 80 embryos.

When Zic3 mRNA was injected into dorsoanimal blastomeres, heads of the embryos were enlarged, and the eyes showed abnormalities in the neuroepithelium of retina, diminishing of retinal pigment cells and loss of lens (these changes are the same as observed in the embryos injected at two-cell stage) (58/80 embryos tested) (FIG. 5G). In the anterior region, neural tube closure was delayed. Pigment cells were found in the dorsal head (58/80 embryos tested).

In contrast, when Zic3 MRNA was injected into ventroanimal blastomeres, clusters of ectopic pigment cells appeared in the ventral epidermis (90/111 embryos tested). The clusters of the ventral pigment cells were arranged remarkably on the ridge of the hyperplastic tissue which transverses the ventral side. These pigment cells were considered to be melanocytes which are derived from the neural crest. Therefore, the inventors performed in situ hybridization of Zic3 MRNA injected embryos using a neural crest marker Xtwi as a probe. The in situ hybridization techniques used were the same as described in (1) above.

As a result, ectopic Xtwi expression was observed near the ectopically appearing clusters of pigment cells in addition to the expansion of the Xtwi-expressing region in the cephalic neural crest.

(5) The Role of Zic3 in Early Embryogeny

In order to examine how the overexpression of Zic3 alters cell fate in early stage embryos, the inventors tested the expression of NCAM, Xtwi, Xslu and EpA (an epidermal antigen gene) [Jones, E. A. & Woodland, H. R.: Cell 44:345–355 (1986)] in early neurulas.

Briefly, a total of 100 pg of Zic3 mRNA was injected into a blastomere of two-cell stage embryos. The expression patterns of the above genes were examined at stage 14 by in situ hybridization using NCAM and Xslu probes and by immunohistochemical staining using EpA monoclonal antibody (obtained from Mr. E. Jones of Univ. of Warwick, UK).

Figure 6:
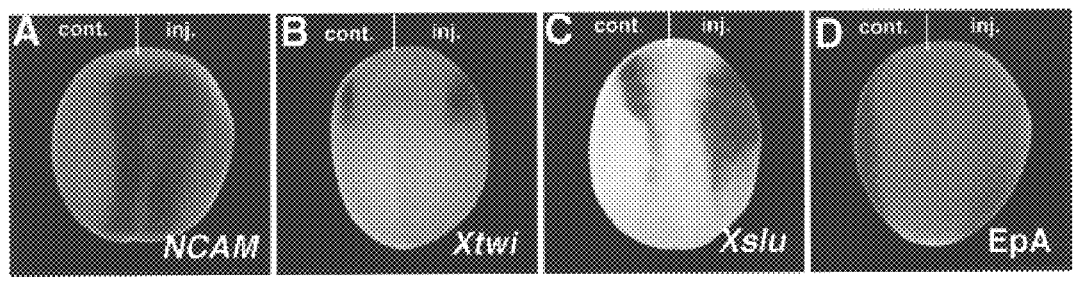
FIGS. 6A–6D present photographs showing the results of expression analysis of the Zic3 gene (morphology of an organism).

The results are shown in FIG. 6., where each panel shows a dorsal view of a stage 14 embryo. Panel A, panel B and panel C show the results when NCAM, Xtwi and Xslu were used as a probe, respectively. Panel D shows the results when EpA monoclonal antibody was used.

NCAM expression increased markedly in the anterior neural plate region of the Zic3 mRNA injected side (31/45 embryos tested) (FIG. 6A). Xtwi (43/45 embryos tested) and Xslu (12/12 embryos tested) expression in neural crest cells was also increased by the injection (FIG. 6B and C). However, in the Zic3 mRNA injected site of the epidermis, EpA staining was decreased (FIG. 6D).

If it is assumed that epidermal fate changes into neural and neural crest fate as a result of the injection of Zic3 MRNA, the epidermis should be reduced at the site of Zic3 mRNA injection. To test this possibility, the inventors determined the expression of EpA in Zic3 mRNA injected embryos.

diaminobenzidine and 0.02% $H_2O_2$). After a color of an appropriate density was formed, the embryos were washed with 100% methanol for 10 min twice. Subsequently, the embryos were dipped in BABB solution (benzyl alcohol:benzylbenzoate=1:2) to make them transparent, followed by storing in 100% methanol.

As a result, expression of EpA was significantly reduced in the Zic3 injected site (FIG. 6D) . This fact indicates that Zic3 alters epidermal cell fate int o neural and neural crest cell fate.

(6) Function Expression Test for Zic3

The above studies suggest that Zic3 plays important roles in early neural and neural crest development. In order to examine how Zic3 acts in these processes, the inventors tested the expression of several marker genes by RT-PCR in Zic3 mRNA injected ani mal cap explants.

One hundred pg of Zic3 or LacZ mRNA (control) was injected into two-cell stage embryos. The animal cap of each embryo was explanted at stage 9 and cultured.

When the sibling embryos reached stage 20, the expression of neural marker genes (NCAM, Neurogenin, NeuroD, XASH-3, XATH-3, XlPOU 2) and neural crest markers (Xtwi, Xslu) was examined by RT-PCR. Also, the ex pression of an early mesodermal marker Xbra (Xenopus brachyury) and a dorsal mesodermal marker M. actin (muscle actin) was examined by RT-PCR when the sibling embryos reached stage 10.5 and stage 20, respectively, in the same manner as describe above. For Neurogenin, Xbra and M. actin, an RT-PCR was performed using the following primers.

```
Neurogenin  (sense)      5'-CAAGAGCGGAGAAACTGTGT-3'  (SEQ ID NO:31)
            (antisense)  5'-GAAGGAGCAACAAGAGGAAG-3'  (SEQ ID NO:32)
Xbra        (sense)      5'-GTCCGTACACTCACAGAAAC-3'  (SEQ ID NO:33)
            (antisense)  5'-GAGGTGTAGAGCCAAGTAAG-3'  (SEQ ID NO:34)
M. actin    (sense)      5'-GCTGACAGAATGCAGAAG-3'    (SEQ ID NO:35)
            (antisense)  5'-TTGCTTGGAGGAGTGTGT-3'    (SEQ ID NO:36)
```

Figure 7:
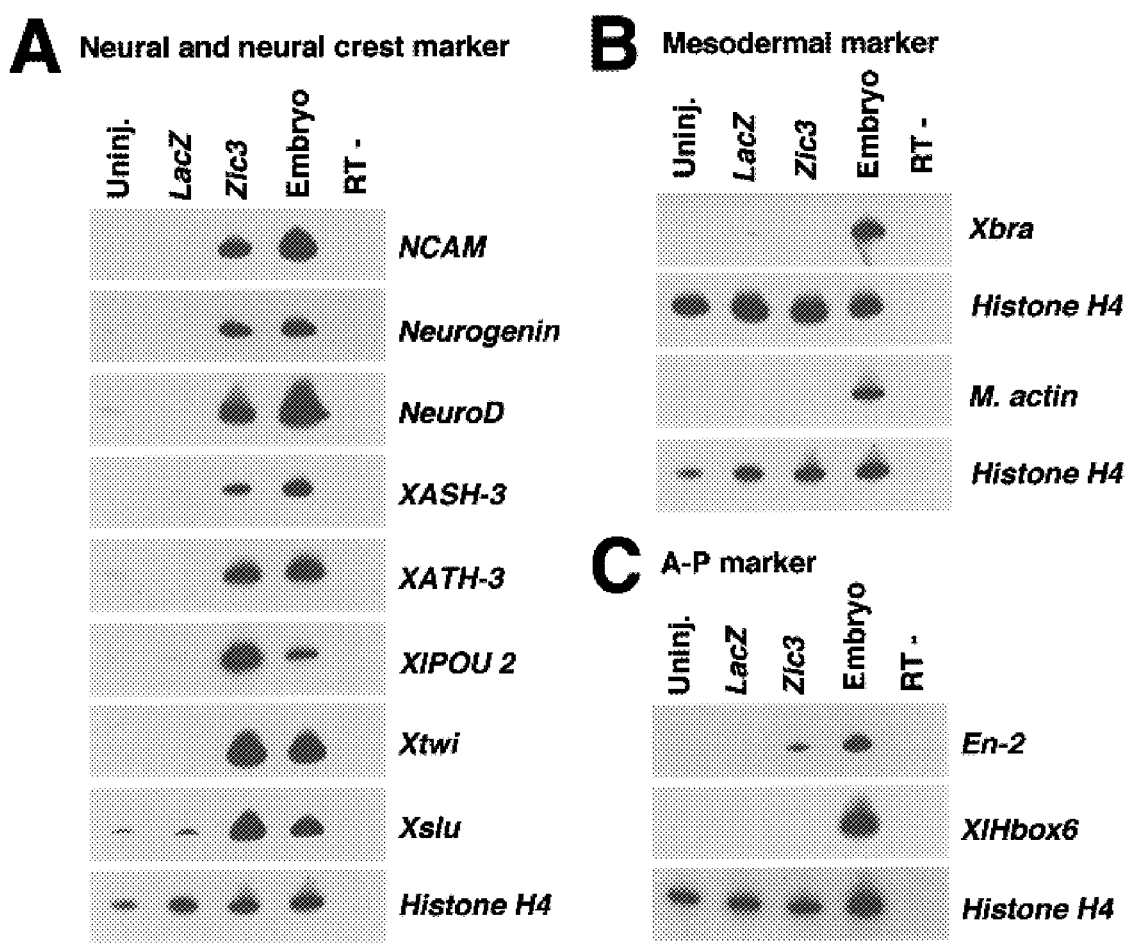
FIGS. 7A, 7B, and 7C present autoradiographs showing the results of expression analysis of the Zic3 gene.

The expression was determined as described below. Briefly, embryos were dipped in Dent's fixative (20% dimethyl sulfoxide, 80% methanol) and shaken gently several times. Then, they were left at –20° C. overnight for fixation. After removal of the fixative, a bleach (10% $H_2O_2$, 47% methanol, 20% DMSO) was added to the embryos, which were then allowed to stand for 1 to 2 days for bleaching. After removal of the bleach, 100% methanol was added to the embryos, which were then stored at –20° C. Thereafter, the embryos were washed with TBS (50 mM Tris-HCl (pH 7.5), 150 mM NaCl, 0.05% Tween 20) for 20 min twice. On the other hand, EpA monoclonal antibody was diluted to 1/100 to 1/1000 with TBS containing 20% normal goat serum. Using the resultant dilution, the embryos were primarily stained at 4° C. overnight. Subsequently, the embryos were washed with TBS for 1 hr 5 times. Then, using ca. 200 fold dilution of peroxidase-conjugated secondary antibody in TBS containing 20% normal goat serum, the embryos were secondarily stained at 4° C. overnight. After 1 hr staining with TBS 5 times, the embryos were secondarily stained with a coloring solution (TBS containing 0.5 mg/ml The results are shown in FIG. 7. Zic3 induced all of the neural and neural crest marker genes tested. Although uninjected (Uninj.) or LacZ injected (LacZ) caps did not express any of these markers, animal caps injected with Zic3 mRNA (Zic3) expressed all of the neural and neural crest marker genes tested (FIG. 7A). However, Zic3 did not induce mesodermal markers (FIG. 7B).

These results demonstrate that Zic3 is able to direct the induction of neural tissues except mesoderm and that Zic3 is able to change directly the epidermal fate of cells to neural and neural crest fate.

Further, the inventors tested the expression of a molecular marker En-2 expressed in anterior neural plate [Hemmati-Brivanlou, A. et al., Development 111:715–724 (1991)] and a posterior marker XlHbox6 [Wright, C. V. E. et al., Development 109:225–234 (1990)] by RT-PCR in the same manner as described above. For En-2 and XlHbox6, an RT-PCR was performed using the following primers.

```
En-2      (sense)      5'-CACAAGGGGTTAAAGGCAAG-3' (SEQ ID NO:37)

(antisense)  5'-CCCAGTGTCTCTCTCAGTAT-3' (SEQ ID NO:38)

XlHbox6   (sense)      5'-TACTTACGGGCTTGGCTGGA-3' (SEQ ID NO:39)

(antisense)  5'-AGCGTGTAACCAGTTGGCTG-3' (SEQ ID NO:40)
```

As a result, though the anterior neural marker En-2 was induced, the posterior marker XlHbox6 was not induced (FIG. 7C). This result is consistent with the previous finding that the neural tissue generated by the blockage of BMP4 signals is anterior neuroectoderm [Hemmati-Brivanlou, A. et al., Cell 77:283–295 (1994); Sasai, Y. et al., Nature 376:333–336 (1995); Lamb, T. M. et al., Science 262:713–718 (1993)]. Therefore, it has become clear that Zic3 has an activity to induce anterior neuroectoderm.

Figure 4:
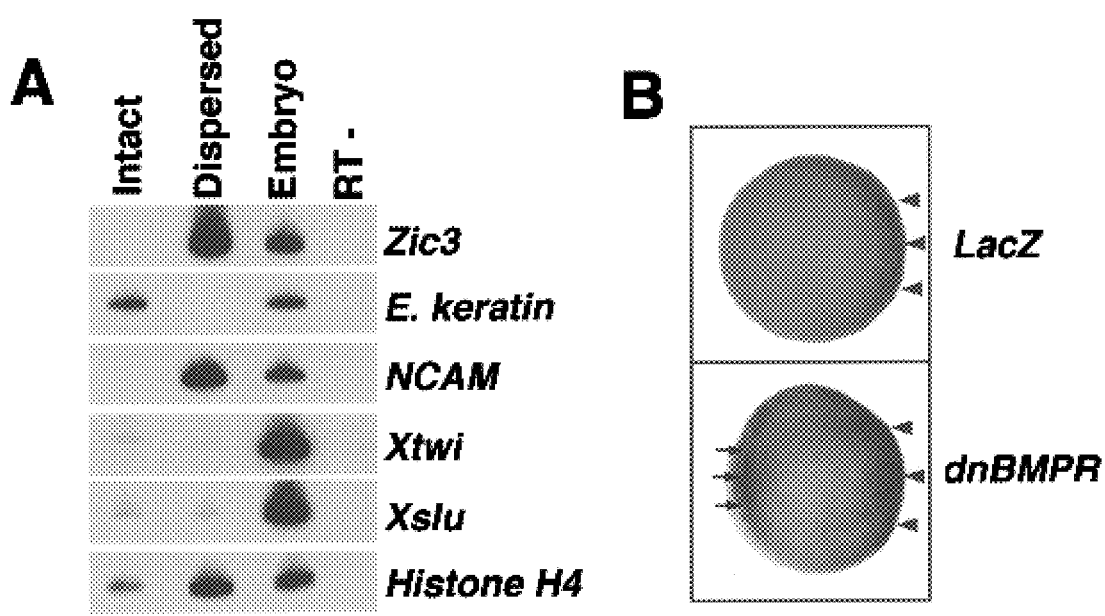
FIGS. 4A and 4B present autoradiographs showing the results of expression analysis of the Zic3 gene and photographs showing morphology of an organism.

Zic3 overexpression induced the neural marker NCAM and the neural crest markers Xtwi and Xslu in explants (FIG. 7A). This presents a contrast to the result that Zic3 was expressed but Xtwi and Xslu were not in dispersed animal cap cells (FIG. 4).

From the results described above, it has been shown that Zic3 induces the proneural genes and that Zic3 acts upstream of these proneural genes reported to date. Therefore, Zic3 has neurogenesis inducing activity, in particular early neurogenesis inducing activity and thus can be called a master gene for neural induction.

What is claimed is:

1. An isolated nucleotide sequence as set forth in SEQ ID NO: 1, which encodes a neurogenesis-inducing protein.

2. An isolated nucleotide sequence encoding a protein having the amino acid sequence set forth in SEQ ID NO: 2.

3. A recombinant vector comprising the nucleotide sequence of claim 1.

4. A host cell comprising the recombinant vector of claim 3.

5. An in vitro method for producing a neurogenesis-inducing protein, comprising the steps of:
   a) providing:
      i) the recombinant vector of claim 3, and
      ii) a host cell;
   b) introducing said vector into said host cell to produce a transformed cell which contains said recombinant vector and expresses said neurogenesis-inducing protein; and c) culturing said transformed cell to produce said neurogenesis-inducing protein.

6. The method of claim 5, further comprising the step of:
d) isolating said neurogenesis inducing protein.

7. The recombinant vector of claim 3, wherein said vector comprises in operable linkage a promoter and a vector backbone, wherein said vector backbone is a viral nucleotide sequence selected from the group consisting of adenovirus, adeno-associated virus, herpes virus, vaccinia virus and retrovirus.

8. A composition comprising the recombinant vector of claim 3 and liposomes.

9. A method of inducing early neurogenesis in a *Xenopus laevis* embryo comprising:
(a) providing a two-cell to eight-cell stage *Xenopus laevis* embryo;
(b) providing an amount of MnRNA encoding the polypeptide of SEQ ID NO:2, wherein said amount is sufficient to induce early neurogenesis when injected into at least one blastomere of said two-cell stage to eight-cell stage embryo; and,
(c) injecting said mRNA into at least one blastomere of said two-cell stage to eight-cell stage embryo such that early neurogenesis ensues as the embryo develops, wherein the early neurogenesis results in at least one characteristic selected from the group consisting of: alteration of epidermal cell fate to neural or neural crest cell fate; thickening of neural walls relative to those in untreated tissue; distortion of a neural retina; reduction of retinal pigment; an increase in expression of neurogenesis markers including NCAM, Xtwi, Xslu, Neurogenin, NeuroD, XASH-3, XATH-3, XlPOU2, or En-2; and a decrease in expression of the epidermal cell marker EpA.

* * * * *

SEQUENCE LISTING

```
<160> NUMBER OF SEQ ID NOS: 40

<210> SEQ ID NO 1
<211> LENGTH: 2364
<212> TYPE: DNA
<213> ORGANISM: Xenopus laevis
<220> FEATURE:
<221> NAME/KEY: CDS
<222> LOCATION: (138)..(1463)

<400> SEQUENCE: 1
ctcagttgga gagggtgaac tgtttccagg attttcggaa gcaaaaggaa ttaaaagata        60 acttttccc cccgaacatt ccacatgaac tgtatccagt gctgaccaca gatcagcttg        120
tactgctcag ctcattc atg aca atg cta tta gat gga gga ccg cag ttt        170
                   Met Thr Met Leu Leu Asp Gly Gly Pro Gln Phe
                    1               5                      10 ccc acc ctg gga gtt cgt ggg ttt ggg aca gct cgc cat cat gag atg        218
Pro Thr Leu Gly Val Arg Gly Phe Gly Thr Ala Arg His His Glu Met
            15                  20                  25 tcc aac cga gat gct ggc atg ggg ctt aat cca ttc act gag cct tct        266
Ser Asn Arg Asp Ala Gly Met Gly Leu Asn Pro Phe Thr Glu Pro Ser
        30                  35                  40 cat gct gcg gct ttt aag ctc agt cca gca agt cat gat ctt tct tca        314
His Ala Ala Ala Phe Lys Leu Ser Pro Ala Ser His Asp Leu Ser Ser
    45                  50                  55 agc cag agc tca gct ttt acc cca cag gct tct gga tat gcc aat tca        362
Ser Gln Ser Ser Ala Phe Thr Pro Gln Ala Ser Gly Tyr Ala Asn Ser
60                  65                  70                  75 ctt gga cat cat gct ggg cag gtg cca tct tac ggt ggt gca gcc ttt        410
Leu Gly His His Ala Gly Gln Val Pro Ser Tyr Gly Gly Ala Ala Phe
                80                  85                  90 aac tca aca cgc gat ttc ctt ttc cga aat cgt aac tct gga att gca        458
Asn Ser Thr Arg Asp Phe Leu Phe Arg Asn Arg Asn Ser Gly Ile Ala
            95                  100                 105 gac tca tct tct gca ggc agt caa cat gga ctt ttt gcc aac cat ggg        506
Asp Ser Ser Ser Ala Gly Ser Gln His Gly Leu Phe Ala Asn His Gly
        110                 115                 120 ccc cca gga att ggt gag ccc cca gga cac ctg atc ttc ccc gga ctt        554
Pro Pro Gly Ile Gly Glu Pro Pro Gly His Leu Ile Phe Pro Gly Leu
```

```
                    125                 130                 135
cat gag caa agt tcc agc cat aca tca tcc aat gga cat gtg gtc aat       602
His Glu Gln Ser Ser Ser His Thr Ser Ser Asn Gly His Val Val Asn
140                 145                 150                 155 ggt caa atg cat tta gga ctc aga gga gat att ttc gga cgt cca gat       650
Gly Gln Met His Leu Gly Leu Arg Gly Asp Ile Phe Gly Arg Pro Asp
                160                 165                 170 cct tat agg gca gtg ccc agc ccg agg aca gat cat tat gct gct gcc       698
Pro Tyr Arg Ala Val Pro Ser Pro Arg Thr Asp His Tyr Ala Ala Ala
            175                 180                 185 caa ttc cat aat tat aat cac atg aat atg agc atg aat gta gct gct       746
Gln Phe His Asn Tyr Asn His Met Asn Met Ser Met Asn Val Ala Ala
        190                 195                 200 cac cat ggc ccc ggg gct ttc ttt aga tac atg agg caa ccc atc aaa       794
His His Gly Pro Gly Ala Phe Phe Arg Tyr Met Arg Gln Pro Ile Lys
    205                 210                 215 caa gag tta tcg tgt aaa tgg ctt gag gaa tca aca atg aac cat cct       842
Gln Glu Leu Ser Cys Lys Trp Leu Glu Glu Ser Thr Met Asn His Pro
220                 225                 230                 235 cag aaa acc tgt gac agg aca ttt agc agc atg cat gaa ctg gtt aca       890
Gln Lys Thr Cys Asp Arg Thr Phe Ser Ser Met His Glu Leu Val Thr
                240                 245                 250 cat atg aca atg gaa cat gtt ggg ggt cca gaa caa aat aat cac ata       938
His Met Thr Met Glu His Val Gly Gly Pro Glu Gln Asn Asn His Ile
            255                 260                 265 tgc tac tgg gag gaa tgt ccc agg gga ggt aaa tct ttt aaa gca aag       986
Cys Tyr Trp Glu Glu Cys Pro Arg Gly Gly Lys Ser Phe Lys Ala Lys
        270                 275                 280 tat aaa cta gtg aat cat atc agg gtg cat acc gga gaa aaa ccc ttt      1034
Tyr Lys Leu Val Asn His Ile Arg Val His Thr Gly Glu Lys Pro Phe
    285                 290                 295 cca tgc ccc ttc cct gga tgt ggg aaa atc ttt gca cgt tca gaa aat      1082
Pro Cys Pro Phe Pro Gly Cys Gly Lys Ile Phe Ala Arg Ser Glu Asn
300                 305                 310                 315 ctc aag atc cac aaa aga act cat aca ggt gag aag cca ttc aag tgt      1130
Leu Lys Ile His Lys Arg Thr His Thr Gly Glu Lys Pro Phe Lys Cys
                320                 325                 330 gag ttt gaa ggc tgc gat aga agg ttt gca aac agc agc gac agg aaa      1178
Glu Phe Glu Gly Cys Asp Arg Arg Phe Ala Asn Ser Ser Asp Arg Lys
            335                 340                 345 aaa cat atg cat gtg cac acg tca gat aag cca tat atc tgc aaa gtg      1226
Lys His Met His Val His Thr Ser Asp Lys Pro Tyr Ile Cys Lys Val
        350                 355                 360 tgt gat aaa tcc tac act cac ccc agc tcc cta aga aag cac atg aag      1274
Cys Asp Lys Ser Tyr Thr His Pro Ser Ser Leu Arg Lys His Met Lys
    365                 370                 375 gtt cat gaa tca caa ggg tct gat tct tcc cct gct gcc agc tca ggg      1322
Val His Glu Ser Gln Gly Ser Asp Ser Ser Pro Ala Ala Ser Ser Gly
380                 385                 390                 395 tac gaa tct gct acc cca cca gca atg gtt tct gcc aac agt gag gaa      1370
Tyr Glu Ser Ala Thr Pro Pro Ala Met Val Ser Ala Asn Ser Glu Glu
                400                 405                 410 cct tcc aaa aat tca tca gca aca cat cag act aac aac aat tct cat      1418
Pro Ser Lys Asn Ser Ser Ala Thr His Gln Thr Asn Asn Asn Ser His
            415                 420                 425 aac aca gga cta ctt cca cct aat ttt aac gaa tgg tat gtc tga           1463
Asn Thr Gly Leu Leu Pro Pro Asn Phe Asn Glu Trp Tyr Val
        430                 435                 440 gcaaaatgta gagaggccta gtcatgctca acaaaaggac catgtgcaaa aaacagaat     1523
```

-continued

```
ccaattttt  ttatgttgaa  ccaaggcgga  aatggaattt  accacacaag  caacagtata   1583
gggcttcatc  ttgttaaaat  aatttaccaa  cattttctaa  agatggctac  agactaacaa   1643 agccctttc  tcaggatctg  aacacatttt  ttggtgtttg  tatttcctct  gattttatgc   1703
ccttttcatt  ttaacaactt  cactccttt  ttttttttt  aaagaaatta  agaggtcttt   1763
agctaatgta  cttaaaattc  tcttcacctt  tgtggtgaat  gttaaactct  cacattctta   1823
aacagtgcca  aagtcttgtt  atttcttgaa  cctaactcaa  agcattacac  ttgtgaatgt   1883
attccttgtc  ttatagggtc  aaagctgttg  tgtggcatat  tttcagaaat  gggaatgtga   1943
tgttcataca  cagattgtga  ccatttagta  cagttgcctt  tgtaagaac  ttttgtaaat   2003 acttatccac  gatgccatat  atttatcatt  tgtaattaaa  ttattgatac  aagtgccggg   2063
aactgaacaa  tatttatgag  aaaaaaagtt  tttctaacaa  aactctgtat  agcttttggt   2123
tataactgct  ttagcattaa  aaatgattgt  tttgaagaat  tcccatttaa  gctgtctaac   2183
aaatgtttgt  ttacgtcatg  caatgctgaa  actaatgaca  atattctgat  tctgctgtat   2243
taattggtca  tcaaaaacta  taattttca  gcttgtttga  gcaatacttg  tagatatata   2303
aaatatttaa  gataaaatcc  tatttatttt  gaagaataaa  gtaactgaa  agtacttgtt   2363 g                                                                        2364
```

<210> SEQ ID NO 2
<211> LENGTH: 441
<212> TYPE: PRT
<213> ORGANISM: Xenopus laevis

<400> SEQUENCE: 2

```
Met Thr Met Leu Leu Asp Gly Gly Pro Gln Phe Pro Thr Leu Gly Val
  1               5                  10                  15

Arg Gly Phe Gly Thr Ala Arg His His Glu Met Ser Asn Arg Asp Ala
             20                  25                  30

Gly Met Gly Leu Asn Pro Phe Thr Glu Pro Ser His Ala Ala Ala Phe
         35                  40                  45

Lys Leu Ser Pro Ala Ser His Asp Leu Ser Ser Gln Ser Ser Ala
     50                  55                  60

Phe Thr Pro Gln Ala Ser Gly Tyr Ala Asn Ser Leu Gly His His Ala
 65                  70                  75                  80

Gly Gln Val Pro Ser Tyr Gly Ala Ala Phe Asn Ser Thr Arg Asp
             85                  90                  95

Phe Leu Phe Arg Asn Arg Asn Ser Gly Ile Ala Asp Ser Ser Ser Ala
            100                 105                 110

Gly Ser Gln His Gly Leu Phe Ala Asn His Gly Pro Pro Gly Ile Gly
        115                 120                 125

Glu Pro Pro Gly His Leu Ile Phe Pro Gly Leu His Glu Gln Ser Ser
    130                 135                 140

Ser His Thr Ser Ser Asn Gly His Val Val Asn Gly Gln Met His Leu
145                 150                 155                 160

Gly Leu Arg Gly Asp Ile Phe Gly Arg Pro Asp Pro Tyr Arg Ala Val
                165                 170                 175

Pro Ser Pro Arg Thr Asp His Tyr Ala Ala Ala Gln Phe His Asn Tyr
            180                 185                 190

Asn His Met Asn Met Ser Met Asn Val Ala Ala His Gly Pro Gly
        195                 200                 205

Ala Phe Phe Arg Tyr Met Arg Gln Pro Ile Lys Gln Glu Leu Ser Cys
```

-continued

```
            210                 215                 220
Lys Trp Leu Glu Glu Ser Thr Met Asn His Pro Gln Lys Thr Cys Asp
225                 230                 235                 240

Arg Thr Phe Ser Ser Met His Glu Leu Val Thr His Met Thr Met Glu
                245                 250                 255

His Val Gly Gly Pro Glu Gln Asn Asn His Ile Cys Tyr Trp Glu Glu
                260                 265                 270

Cys Pro Arg Gly Gly Lys Ser Phe Lys Ala Lys Tyr Lys Leu Val Asn
            275                 280                 285

His Ile Arg Val His Thr Gly Glu Lys Pro Phe Pro Cys Pro Phe Pro
        290                 295                 300

Gly Cys Gly Lys Ile Phe Ala Arg Ser Glu Asn Leu Lys Ile His Lys
305                 310                 315                 320

Arg Thr His Thr Gly Glu Lys Pro Phe Lys Cys Glu Phe Glu Gly Cys
                325                 330                 335

Asp Arg Arg Phe Ala Asn Ser Ser Asp Arg Lys Lys His Met His Val
                340                 345                 350

His Thr Ser Asp Lys Pro Tyr Ile Cys Lys Val Cys Asp Lys Ser Tyr
            355                 360                 365

Thr His Pro Ser Ser Leu Arg Lys His Met Lys Val His Glu Ser Gln
        370                 375                 380

Gly Ser Asp Ser Ser Pro Ala Ala Ser Ser Gly Tyr Glu Ser Ala Thr
385                 390                 395                 400

Pro Pro Ala Met Val Ser Ala Asn Ser Glu Glu Pro Ser Lys Asn Ser
                405                 410                 415

Ser Ala Thr His Gln Thr Asn Asn Asn Ser His Asn Thr Gly Leu Leu
                420                 425                 430

Pro Pro Asn Phe Asn Glu Trp Tyr Val
            435                 440
```

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Designed peptide based on amino acid sequence of zinc finger motif of mouse Zic gene family.

<400> SEQUENCE: 3

```
Glu Asn Leu Lys Ile His Lys
  1               5
```

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Designed peptide based on amino acid sequence of zinc finger motif of mouse Zic gene family.

<400> SEQUENCE: 4

```
His Met Lys Val His Glu Glu
  1               5
```

<210> SEQ ID NO 5
<211> LENGTH: 20
<212> TYPE: DNA
<213> ORGANISM: Artificial Sequence

```
<220> FEATURE:
<223> OTHER INFORMATION: Description of Artificial Sequence: Synthetic
      DNA

<400> SEQUENCE: 5
gagaacctca agatccacaa                                                    20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 6
ttyccatgra ccttcatgtg                                                    20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 7
ttctcaggat ctgaacacat                                                    20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 8
ccctataaga caaggaatac                                                    20

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 9
ggactctcgc cttgtggc                                                      18

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 10
gatatgttct tgtaatagtc agt                                                23

<210> SEQ ID NO 11
<211> LENGTH: 19
<212> TYPE: DNA
<213> ORGANISM: Artificial Sequence
<220> FEATURE:
```

```
<223> OTHER INFORMATION: Description of Artificial Sequence:  Synthetic
      DNA

<400> SEQUENCE: 11
tggacctcag gccatgttc                                                    19

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence:  Synthetic
      DNA

<400> SEQUENCE: 12
gatgctgagt ggaggtgtta                                                   20

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence:  Synthetic
      DNA

<400> SEQUENCE: 13
acccaacgac cacgtggacc tg                                                22

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence:  Synthetic
      DNA

<400> SEQUENCE: 14
agctcattgc aggaggtgtc tg                                                22

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence:  Synthetic
      DNA

<400> SEQUENCE: 15
gtgaaatccc aatagacacc                                                   20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence:  Synthetic
      DNA

<400> SEQUENCE: 16
ttccccatat ctaaaggcag                                                   20

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence:  Synthetic
```

DNA

<400> SEQUENCE: 17
cacagttcca ccaaatgc                                                    18

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence:  Synthetic
      DNA

<400> SEQUENCE: 18
ggaatcaagc ggtacaga                                                    18

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence:  Synthetic
      DNA

<400> SEQUENCE: 19
acacggcatt gatcctacag                                                  20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence:  Synthetic
      DNA

<400> SEQUENCE: 20
agctccttcg gtgtaatgac                                                  20

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence:  Synthetic
      DNA

<400> SEQUENCE: 21
cgggataaca ttcagggtat cact                                             24

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence:  Synthetic
      DNA

<400> SEQUENCE: 22
atccatggcg gtaactgtct tcct                                             24

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence:  Synthetic
      DNA

```
<400> SEQUENCE: 23
aactgccagg actggatggt                                              20

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 24
ggcaggattt agagttgctt c                                            21

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 25
caccagaaca cagagtac                                                18

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 26
caaccttccc atcaacca                                                18

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 27
agtccgatct cagtgaaggg ca                                           22

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 28
tgtgtgtggc ctgagctgta g                                            21

<210> SEQ ID NO 29
<211> LENGTH: 18
<212> TYPE: DNA
<213> ORGANISM: Artificial Sequence
<220> FEATURE:
<223> OTHER INFORMATION: Description of Artificial Sequence: Synthetic
      DNA
```

<400> SEQUENCE: 29
gccctatttc cttgttgc                                                          18

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 30 aaccettctt ggttgcac                                                          18

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 31
caagagcgga gaaactgtgt                                                        20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 32
gaaggagcaa caagaggaag                                                        20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 33
gtccgtacac tcacagaaac                                                        20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 34
gaggtgtaga gccaagtaag                                                        20

<210> SEQ ID NO 35
<211> LENGTH: 18
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 35

```
gctgacagaa tgcagaag                                                18

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence:  Synthetic
      DNA

<400> SEQUENCE: 36
ttgcttggag gagtgtgt                                                18

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence:  Synthetic
      DNA

<400> SEQUENCE: 37
cacaaggggt taaaggcaag                                              20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence:  Synthetic
      DNA

<400> SEQUENCE: 38
cccagtgtct ctctcagtat                                              20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence:  Synthetic
      DNA

<400> SEQUENCE: 39
tacttacggg cttggctgga                                              20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence:  Synthetic
      DNA

<400> SEQUENCE: 40
agcgtgtaac cagttggctg                                              20
```